United States Patent
Lind et al.

(10) Patent No.: US 10,716,799 B2
(45) Date of Patent: *Jul. 21, 2020

(54) PHARMACEUTICAL SPRAY COMPOSITION COMPRISING A VITAMIN D ANALOGUE AND A CORTICOSTEROID

(71) Applicant: LEO Pharma A/S, Ballerup (DK)

(72) Inventors: Marianne Lind, Bagsværd (DK); Gritt Rasmussen, Virum (DK); Mette Rydahl Sonne, Brøndby Strand (DK); Jens Hansen, Virum (DK); Karsten Petersson, Ballerup (DK)

(73) Assignee: LEO Pharma A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/554,586

(22) Filed: Aug. 28, 2019

(65) Prior Publication Data
US 2019/0381074 A1 Dec. 19, 2019

Related U.S. Application Data

(63) Continuation of application No. 16/135,366, filed on Sep. 19, 2018, now Pat. No. 10,660,908, which is a continuation of application No. 14/707,733, filed on May 8, 2015, now Pat. No. 10,130,640, which is a continuation of application No. 13/703,214, filed as application No. PCT/DK2011/000060 on Jun. 10, 2011, now Pat. No. 9,119,781.

(60) Provisional application No. 61/353,893, filed on Jun. 11, 2010.

(51) Int. Cl.
| | |
|---|---|
| A61K 31/593 | (2006.01) |
| A61K 31/59 | (2006.01) |
| A61K 47/06 | (2006.01) |
| A61K 47/08 | (2006.01) |
| A61M 11/00 | (2006.01) |
| A61K 9/00 | (2006.01) |
| A61K 9/12 | (2006.01) |
| A61K 31/573 | (2006.01) |
| A61K 31/58 | (2006.01) |
| A61M 35/00 | (2006.01) |
| A61K 47/14 | (2017.01) |
| A61K 47/22 | (2006.01) |
| B65D 83/20 | (2006.01) |
| B65D 83/14 | (2006.01) |

(52) U.S. Cl.
CPC .......... *A61K 31/593* (2013.01); *A61K 9/0014* (2013.01); *A61K 9/122* (2013.01); *A61K 9/124* (2013.01); *A61K 31/573* (2013.01); *A61K 31/58* (2013.01); *A61K 31/59* (2013.01); *A61K 47/06* (2013.01); *A61K 47/08* (2013.01); *A61K 47/14* (2013.01); *A61K 47/22* (2013.01); *A61M 11/00* (2013.01); *A61M 35/003* (2013.01); *A61M 2210/04* (2013.01); *B65D 83/207* (2013.01); *B65D 83/752* (2013.01)

(58) Field of Classification Search
CPC .. A61K 9/0014; A61K 8/046; A61K 2800/31; A61K 9/124; A61K 47/22; A61K 47/44; A61K 31/00; A61K 31/355; A61K 2800/522; A61K 9/7015; A61Q 19/00; A61P 17/00; A61P 17/02
See application file for complete search history.

(56) References Cited

U.S. PATENT DOCUMENTS

| | | | |
|---|---|---|---|
| 3,722,753 A | 3/1973 | Miles | |
| 4,087,026 A | 5/1978 | Petterson | |
| 4,122,978 A | 10/1978 | Guimind et al. | |
| 5,098,694 A * | 3/1992 | Komp .................. | A61K 8/36 424/47 |
| 5,439,670 A | 8/1995 | Purewal et al. | |
| 5,635,165 A | 6/1997 | Panitch | |
| 5,976,504 A | 11/1999 | Russell | |
| 5,990,100 A | 11/1999 | Rosenburg et al. | |
| 6,228,346 B1 | 5/2001 | Zhang et al. | |
| 6,753,013 B1 † | 6/2004 | Didriksen | |
| 2004/0213744 A1 | 10/2004 | Lulla et al. | |
| 2005/0281749 A1 | 12/2005 | Willcox et al. | |
| 2005/0281754 A1 | 12/2005 | Willcox et al. | |
| 2005/0281755 A1 | 12/2005 | Zarif et al. | |
| 2006/0102661 A1 | 5/2006 | Scheindel | |
| 2006/0275218 A1 | 12/2006 | Tamarkin et al. | |
| 2007/0181608 A1 | 8/2007 | Meshberg | |

(Continued)

FOREIGN PATENT DOCUMENTS

| | | |
|---|---|---|
| EP | 1457196 A1 | 9/2004 |
| IN | 201621031611 | 6/2019 |

(Continued)

OTHER PUBLICATIONS

Alfresa Pharma Corporation (Manufacturing Vendor), "LEDERCORT," Triamcinolone Acetonide formulation, Japan Standard Product Classification No. 872646, Pharmaceutical Interview Form, Version 6—Revised Apr. 2015, Earliest Release date: Aug. 1, 1961, 3 pages.
Astellas Pharma Inc. (Manufacturer), "Diflal®," Diflorasone Diacetate, Japan Standard Product Classification No. 872646, Pharmaceutical Interview Form, Version 9—Revised Apr. 2014, Release date: Sep. 3, 1985, 3 pages.
Barrett et al., "The Effect of Particle Size and Vehicle on the Percutaneous Absorption of Fluocinolone Acetonide," Br. J. Dermatol., vol. 77, 1965, pp. 576-578 (4 pages total).

(Continued)

*Primary Examiner* — Mark V Stevens
(74) *Attorney, Agent, or Firm* — Finnegan, Henderson, Farabow, Garrett & Dunner, LLP

(57) ABSTRACT

The present invention relates to a topical spray composition comprising a biologically active vitamin D derivative or analogue and a corticosteroid, and its use in the treatment of dermal diseases and conditions.

26 Claims, 5 Drawing Sheets

(56) References Cited

U.S. PATENT DOCUMENTS

| | | | |
|---|---|---|---|
| 2007/0196453 | A1 | 8/2007 | Zhang et al. |
| 2007/0196459 | A1* | 8/2007 | Zhang ................. A61K 9/0014 424/448 |
| 2008/0213192 | A1 | 9/2008 | Schlesinger et al. |
| 2008/0234239 | A1* | 9/2008 | Wheeler .............. A61K 9/0014 514/167 |
| 2008/0260655 | A1† | 10/2008 | Tamarkin |
| 2010/0189674 | A1 | 7/2010 | Morrison et al. |
| 2012/0244093 | A1 | 9/2012 | Daniels |

FOREIGN PATENT DOCUMENTS

| | | | |
|---|---|---|---|
| JP | H10-182375 A | 7/1988 | |
| JP | 2772073 B2 | 7/1998 | |
| JP | 2000-063254 A | 2/2000 | |
| JP | 2000-086500 A | 3/2000 | |
| JP | 2002-138015 A | 5/2002 | |
| JP | 2002-241309 A | 8/2002 | |
| JP | 2002-542293 A | 12/2002 | |
| JP | 2003-081812 A | 3/2003 | |
| JP | 2004-512297 A | 4/2004 | |
| JP | 2006-511545 A | 4/2006 | |
| JP | 2007-039465 A | 2/2007 | |
| JP | 3881400 B2 | 2/2007 | |
| JP | 2007-332182 A | 12/2007 | |
| JP | 2008-502645 A | 1/2008 | |
| JP | 2008-502646 A | 1/2008 | |
| JP | 2008-502663 A | 1/2008 | |
| JP | 2008-540508 A | 11/2008 | |
| JP | 2009-519957 A | 5/2009 | |
| JP | 4450545 B2 | 4/2010 | |
| JP | 2013-513558 A | 4/2013 | |
| RU | 2156126 C2 | 9/2000 | |
| RU | 2238734 C2 | 10/2004 | |
| WO | WO-9304671 A1 * | 3/1993 | ............. A61K 9/008 |
| WO | WO 1994/15912 A1 | 7/1994 | |
| WO | WO 1995/04522 A1 | 2/1995 | |
| WO | WO 2000/015193 | 3/2000 | |
| WO | WO 2000/64450 A1 | 11/2000 | |
| WO | WO 2002/34235 A1 | 5/2002 | |
| WO | WO 2004/054588 A1 | 7/2004 | |
| WO | WO 2005/123090 A1 | 12/2005 | |
| WO | WO 2005/123091 A1 | 12/2005 | |
| WO | WO 2006/111426 A1 | 10/2006 | |
| WO | 2006129161 † | 12/2006 | |
| WO | WO 2006/129161 A2 | 12/2006 | |
| WO | WO 2007/054818 A2 | 5/2007 | |
| WO | WO 2007/070694 A2 | 6/2007 | |
| WO | WO 2008/110815 A1 | 9/2008 | |
| WO | WO 2008/141078 A1 | 11/2008 | |
| WO | WO 2008/152444 A2 | 12/2008 | |
| WO | 2009087578 † | 7/2009 | |
| WO | WO 2009/087578 A2 | 7/2009 | |
| WO | WO-2009087578 A2 * | 7/2009 | ............. A61K 8/046 |
| WO | WO 2009/098595 A2 | 8/2009 | |
| WO | WO 2010/042701 A2 | 4/2010 | |

OTHER PUBLICATIONS

Barry, "Mode of Action of Penetration Enhancers in Human Skin," Journal of Controlled Release, vol. 6, 1987, pp. 85-97.
Basse et al., "Enhanced in vitro skin penetration and antipsoriatic effect of fixed combination calcipotriol plus betamethasone dipropionate in an innovative foam vehicle", Poster at 44th Annual ESDR Meeting, Sep. 10-13, 2014, 1 page.
Bjorklund et al., "A water gradient can be used to regulate drug transport across skin," Journal of Controlled Release, vol. 143, 2010 (Published online Jan. 13, 2010), pp. 191-200.
Bristol-Myers Squibb K.K. (Manufacturing Vendor), "Kenalog® in Orabase 0.1 %," Triamcinolone Acetonide Ointment, Japan Standard Product Classification No. 872646, Version 1 O—Revised Apr. 2016 (Revised Aug. 2008), Sale-Starting: Dec. 1966, 4 pages.

Castela et al., "Topical corticosteroids in plaque psoriasis: a systematic review of efficacy and treatment modalities," Journal of the European Academy of Dermatology and Venereology, vol. 26, Suppl. 3, 2012, pp. 36-46.
Catanzaro et al., "Propylene glycol dermatitis", Journal of the American Academy of Dermatology, vol. 24, No. 1, Jan. 1991, pp. 90-95.
Chemical encyclopedia—M., Soviet encyclopedia, Edited by I.L. Knunyants, 1998, 3 pages.
Chugai Pharmaceutical Co., Ltd. (Manufacturing Vendor), "ALFAROL®," Alfacalcidol Formulation, Japan Standard Product Classification No. 873 112, Pharmaceutical Interview Form, Version 8—Revised Sep. 2016, Earliest Release Date: Jan. 8, 1981, 4 pages.
Chugai Pharmaceutical Co., Ltd. (Manufacturing Vendor), "Oxarol®," Maxacalcitol formulation, Japan Standard Product Classification No. 872691, Pharmaceutical Interview Form, Version 13—Revised May 2016, Earliest Release Date: Oct. 11, 2001, 4 pages.
Chugai Pharmaceutical Co., Ltd. (Manufacturing Vendor), "Rocaltrol®," Calcitriol Capsule, Japan Standard Product Classification No. 873112, Pharmaceutical Interview Form, Version 7—Apr. 2015, Release date: May 6, 1986, 3 pages.
Coldman et al., "Enhancement of Percutaneous Absorption by the Use of Volatile: Nonvolatile Systems as Vehicles," Journal of Pharmaceutical Sciences, vol. 58, No. 9, Sep. 1969, pp. 1098-1102.
"Daivobet®", Product Information, Oct. 2014, 4 pages.
"Daivobet®", Summary of Product Characteristics (SPC), 9 pages.
Daivobet® Ointment, Product Information, 2001, 8 pages.
"Dimethyl Ether", Extract from "Handbook of Pharmaceutical Excipients", 6th Edition, 2009, pp. 235 and 236.
Eggermont Amm, et al. "Cutaneous Melanoma", Lancet, 2014, vol. 383, pp. 816-827.
English translation of Japanese Office Action dated Apr. 14, 2015 for Japanese Application No. JP 2013-513558 . 2 pages.
English translation of Russian Office Action dated Apr. 10, 2015, for Russian Application No. 2013100996. 3 pages.
English translation of the Japanese Opposition to Grant of Patent, dated Dec. 26, 2016, for Japanese Patent No. 5945268. 40 pages.
European Notice of Opposition against EP-2579852-81 (European Application No. 11726055), issued Sep. 28, 2015, (Opponent: Pentafarma), 12 pages.
Extended European Search Report dated Mar. 16, 2015, for European Application No. 14190881.4 9 pages.
Feldman et al., "Psoriasis: Improving adherence to topical therapy," J. Am. Acad. Dermatol., vol. 59, No. 6, Dec. 2008 (Published online Oct. 3, 2008), pp. 1009-1016.
Glaxosmithkline K.K. (Manufacturing Vendor), "BETNEVATE®," Betamethasone Valerate formulation, Japan Standard Product Classification No. 872647, Pharmaceutical Interview Form, Version 6—Revised Aug. 2013, Release date: Sep. 25, 2009 3 pages.
Glaxosmithkline K.K. (Manufacturing Vendor), "Dermovate®," Clobetasol Propionate, Japan Standard Product Classification No. 872646, Pharmaceutical Interview Form, Version 5—Revised Sep. 2015, Release date: Apr. 19, 1979, 3 pages.
Glaxosmithkline K.K. (Manufacturing Vendor), "Kindavate®," Clobetasone Butyrate Ointment, Japan Standard Product Classification No. 872646, Pharmaceutical Interview Form, Version 4—Revised May 2016, Release date: Mar. 19, 1984, 4 pages.
Glenmark Pharmaceuticals, S.A., "The Patents Act, 1970 (39 of 1970) & The Patents Rules, 2003", complete specification. (18 pages).
Ghafourian et al., "Validated models for predicting skin penetration from different vehicles," European Journal of Pharmaceutical Sciences, vol. 41, 2010 (Published online Sep. 15, 2010), pp. 612-616.
Guy, "Current Status and Future Prospects of Transdermal Drug Delivery," Pharmaceutical Research, vol. 13, No. 12, 1996, pp. 1765-1769.
Hadgraft et al., "Drug crystallization—implications for topical and transdermal delivery," Expert Opinion on Drug Delivery, vol. 13, No. 6, 2016 (Published online Feb. 3, 2016), pp. 817-830—15 pages total.
Hannuksela et al., "Skin reactions to propylene glycol", Contact Dermatitis, 1975, pp. 112-116.
Hollesen Basse et al., "Enhanced in vitro skin penetration and antipsoriatic effect of fixed combination calcipotriol plus betamethasone

(56) References Cited

OTHER PUBLICATIONS dipropionate in an innovative foam vehicle," Clinical Research, Clinical Trials and Therapeutics, Abstracts, No. 192, 2014, pp. S30-S38, abstract provided only.
Iervolino et al., "Penetration enhancement of ibuprofen from supersaturated solutions through human skin," International Journal of Pharmaceutics, vol. 212, 2001, pp. 131-141.
International Search Report for PCT/DK2011/000060 dated Sep. 22, 2011 5 pages.
Koo et al., "Superior efficacy of calcipotriene and betamethasone dipropionate aerosol foam versus ointment in patients with psoriasis vulgaris—A randomized phase 11 study," Journal of Dermatological Treatment, Early Online. 2015 (Published online Oct. 5, 2015). pp. 1-8—9 pages total.
Koo et al., "Superior efficacy of calcipotriene and betamethasone dipropionate aerosol foam versus ointment in patients with psoriasis vulgaris—A randomized phase II study", Journal of Dermatological Treatment, 2016, 27(2), pp. 120-127.
Kowa Company, Ltd. (Manufacturing Vendor), "LIDOMEX® KOWA," Prednisolone Valerate Acetate formulation, Japan Standard Product Classification No. 872646, Pharmaceutical Interview Form, C Version 7—Oct. 2016, Earliest Release date: Aug. 23, 1982, 4 pages.
Laws et al., "Topical treatment of psoriasis," Expert Opinion on Pharmacotherapy, vol. 11, No. 12, 201 O (Published online Jun. 23, 2010), pp. 1999-2009.
Lifusolum, Dictionary of Medical Substances, 2005, 3 pages.
Lebwohl et al., "Fixed Combination Aersol Foam Calcipotriene 0.005% (Cal) Plus Betamethasone Dipropionate 0.064% (BD) is More Efficacious than Cal or BD Aerosol Foam Alone for Psoriasis Vulgaris: A Randomized, Double-blind, Multicenter, Three-arm. Phase 2 Study," J. Clin. Aesthet. Dermatol., vol. 9, No. 2 Feb. 2016 pp. 34-41 (9 pages total).
Leonardi et al., "Efficacy and Safety of Calcipotriene Plus Betamethasone Dipropionate Aerosol Foam in Patients with Psoriasis Vulgaris—a Randomized Phase III Study (PSO-FAST)," Journal of Drugs in Dermatology, vol. 14, Issue 12, Dec. 2015. pp. 1468-1477.
Marks, "The Stratum Corneum Barrier: The Final Frontier," The Journal of Nutrition, vol. 134, 2004, pp. 2017S-2021S.
Menter et al., "Comparing Clobetasol Propionate 0.05% Spray to Calcipotriene 0.005% Betamethasone Dipropionate 0.064% Ointment for the Treatment of Moderate to Severe Plaque Psoriasis," Journal of Drugs in Dermatology, vol. 8, Issue 1, 2009, pp. 52-57.
Menter et al., "Guidelines of care for the management of psoriasis and psoriatic arthritis, Section 1. Overview of psoriasis and guidelines of care for the treatment of psoriasis with biologics," J. Am. Acad. Dermatol., vol. 58. No. 5, May 2008, pp. 826-850.
Menter et al., "Guidelines of care for the management of psoriasis and psoriatic arthritis, Section 3. Guidelines of care for the management and treatment of psoriasis with topical therapies." J. Am. Acad. Dermatol., vol. 60, No. 4, Apr. 2009, pp. 643-659.
Mitsubishi Tanabe Pharma Corporation (Manufacturing Vendor), "MYSER®," Difluprednate, Japan Standard Product Classification No. 872646, Pharmaceutical Interview Form, Version 8—Revised Apr. 2013, Release date: Jul. 8, 1986, 3 pages.
Mitsubishi Tanabe Pharma Corporation (Manufacturing Vendor), "TOPSYM®," Fluocinonide, Japan Standard Product Classification No. 872646, Pharmaceutical Interview Form, Version 6A—Apr. 2008, Release date: Oct. 1, 1975, 3 pages.
Moser et al., "Supersaturation: Enhancement of Skin Penetration and Permeation of a Lipophilic Drug," Pharmaceutical Research, vol. 18, No. 7, 2001, pp. 1006-1011.
Mylan EPD (Manufacturing Vendor), "Zalucs®," Dexamethasone Valerate, Japan Standard Product Classification No. 872646, Pharmaceutical Interview Form, Version 4—Revised Feb. 2017, Release date: Jun. 19, 1986, 4 pages.
Okayama Taiho Pharmaceutical Co., Ltd. (Manufacturing Vendor), "Methaderm®," Dexamethasone Propionate, Japan Standard Product Classification No. 872646, Pharmaceutical Interview Form, Version 6—Revised Aug. 2013, Earliest Release Date: May 1, 1987, 4 pages.
Ortonne, "Psoriasis: new treatment modality with calcipotriol and betamethasone dipropionate", Nouv. Dermatol., vol. 13, No. 10, 1994, 12 pages.
Partial English translation of "Non-atopic life: Atopy treatment not dependent on steroids," URL: http://nonatopi-life.com/ steroido/ siyoukiken.html, Publication Date Unknown, 2 pages.
Paul et al. "Superior efficacy of the fixed combination calcipotriol plus betamethasone di propionate aerosol foam versus gel. in patients with psoriasis vulgaris—the Phase III PSO-ABLE study," 24th EADV Congress, Poster No. P1724, 2015, 6 slides.
"Primol 352", Medicinal grade White Oil, Product Information Printed from the Website of Exxon Mobile on Mar. 21, 2016; 3 pages.
Queille-Roussel et al., "Efficacy of an Innovative Aerosol Foam Formulation of Fixed Combination Calcipotriol plus Betamethasone Dipropionate in Patients with Psoriasis Vulgaris," Clin. Drug Investig., vol. 35, 2015 (Published online Feb. 24, 2015), pp. 239-245.
Reinholz et al "Cathelicidin LL-37: An Antimicrobial Peptide with a Role in Inflammatory Skin Disease" Annals of Dermatology, 2012, vol. 24, pp. 126-135.
Ruzicka et al., "Comparison of Calcipotriol Monotherapy and a Combination of Calcipotriol and Betamethasone Valerate after 2 Weeks' Treatment with Calcipotriol in the Topical Therapy . . . ," British Journal of Dermatology, vol. 138, 1998, pp. 254-258.
Saraceno et al "Efficacy, safety and quality of life of calcipotriol/ betamethasone dipropionate (Dovobet®) versus calcipotriol (Daivonex®) in the treatment of psoriasis vulgaris: A randomized, multicentre, clinical trial." Journal of Dermatological Treatment, 2007, vol. 18, pp. 361-365.
Santos et al. "Enhanced permeation of fentanyl from supersaturated solutions in a model membrane." International journal of Pharmaceutics, vol. 407, 2011 (Published online Jan. 21, 2011), pp. 72-77.
Sato Pharmaceutical Co., Ltd. (Manufacturing Vendor), "Texmeten®," Diflucortolone Valerate, Japan Standard Product Classification No. 872646, Pharmaceutical Interview Form, Version 2—Revised Dec. 2012, Release date: Mar. 1, 1999, 3 pages.
Schaefer et al., "Skin Barrier: Principles of Percutaneous Absorption," Chapters 5 and 6, S. Karger AG, 1996, pp. 153-310 (85 pages total).
Senyigit et al, "Corticosteroids for Skin Delivery: Challenges and New Formulation Opportunities", In Tech, 2012, Chapter 24, pp. 595-612.
Shionogi & Co., Ltd. (Manufacturing Vendor), "Almeta®," Alclometasone Dipropionate, Japan Standard Product Classification No. 872646, Pharmaceutical Interview Form, Version 13—Revised May 2013, Release date: May 27, 1988, 3 pages.
Shionogi & Co., Ltd. (Manufacturing Vendor), "Fulmeta®," Mometasone furancarboxylate formulation, Japan Standard Product Classification No. 872646, Pharmaceutical Interview Form, Version 11—Revised Apr. 2013, Release date: Nov. 29, 1993, 4 pages.
Shionogi & Co., Ltd. (Manufacturing Vendor), "Predonin®," JP Prednisolone, Japan Standard Product Classification No. 872456, Pharmaceutical Interview Form, Version 14—Revised Apr. 2015, Release date: Mar. 1956, 4 pages.
Shionogi & Co., Ltd. (Manufacturing Vendor), "Rinderon®-DP," Betamethasone Dipropionate formulation, Japan Standard Product Classification No. 872646, Pharmaceutical Interview Form, Version 13—Revised Apr. 2013, Earliest Release date: Feb. 12, 1980, 3 pages.
Schon et al., "Medical Progress: Psoriasis," The New England Journal of Medicine, vol. 352, No. 18, May 5, 2005, pp. 1899-1912.
Smith et al., "Future Perspectives for Penetration Enhancers," Chapter 17.2, CRC Press, Inc., 1995, pp. 481-484.
Smyth HDC, "Propellant-driven metered-dose inhalers for pulmonary drug delivery" Expert Opinion in Drug Delivery, 2005, vol. 2, pp. 53-74.
Surber et al., "The Mystical Effects of Dermatological Vehicles," Dermatology, vol. 210, 2005, pp. 157-168.

(56) References Cited

OTHER PUBLICATIONS

Table identifying various "Corticosteroids" by Trade Name, Release Date, Amount of Solvent and Chemical Formula, Date Unknown, 3 pages.

Table identifying various forms of "Vitamin D" by Product Name, Release Date, Amount of Solvent Required, and Structural Formula, Date Unknown, 2 pages.

Taisho Pharmaceutical Co., Ltd. (Manufacturer), "PANDEL®," Hydrocortisone 17-butyrate 21-propionate, Japan Standard Product Classification No. 872646, Pharmaceutical Interview Form, Version 10—Revised Jul. 2008, Earliest Release date: Feb. 3, 1983, 3 pages.

Taraska et al., "A Novel Aerosol Foam Formulation of Calcipotriol and Betamethasone Has No Impact on HPA Axis and Calcium Homeostasis in Patients With Extensive Psoriasis Vulgaris," Journal of Cutaneous Medicine and Surgery, vol. 20, No. 1, 2016, pp. 44-51.

Teijin Pharma Limited (Manufacturing Vendor), "Bonalfa®," Tacalcitol formulation, Japan Standard Product Classification No. 872691, Pharmaceutical Interview Form, Version 2—Nov. 2006 (Oct. 2006—Novel Form 1 ), 3 pages.

Teikoku Pharmaceutical Co., Ltd. (Manufacturing Vendor), "VISDERM®," Amcinonide, Japan Standard Product Classification No. 872646, Pharmaceutical Interview Form, Version 7—Revised Aug. 2009, Release date: Feb. 22, 1982, 3 pages.

The Ministry of Health, Labour and Welfare, "The Japanese Pharmacopoeia, Seventeenth Edition," English Version, General Notices, Apr. 1, 2016, pp. 2-3 (4 pages total).

Thorneloe et al., "Adherence to medication in patients with psoriasis: a systematic literature review," British Journal of Dermatology, vol. 168, 2013, pp. 20-31.

Torii Pharmaceutical Co., Ltd. (Manufacturing Vendor), "LOCOID®," Hydrocortisone Butyrate, Japan Standard Product Classification No. 872646, Pharmaceutical Interview Form, Version 4—Jul. 2012, Release date: Dec. 2008, 3 pages.

Torii Pharmaceutical Co., Ltd., "ANTEBATE®," Betamethasone Butyrate Propionate Formulation, Japan Standard Product Classification No. 872646, Pharmaceutical Interview Form, Version 5—Revised Jun. 2015, Earliest Release date: Jul. 2002, 5 pages.

Torii Pharmaceutical Co., Ltd., "Dovonex®," Calcipotriol Ointment, Japan Standard Product Classification No. 872691, Pharmaceutical Interview Form, Version 5—Revised Apr. 2014, Release date: Sep. 2009, 3 pages.

Woodford et al., "Bioavailability and Activity of Topical Corticosteriods from a Novel Drug Delivery System, the Aerosol Quick-Break Foam," Journal of Pharmaceutical Sciences, vol. 66, No. 1, Jan. 1977, pp. 99-103.

Yoshindo Inc. (Manufacturing Vendor), "TERRA-CORTRIL®," Oxytetracycline Hydrochloride Ointment (with Hydrocortisone), Japan Standard Product Classification No. 872647, Pharmaceutical Interview Form, Version 1—Nov. 2007, Release date: Sep. 1957, 4 pages.

Zhai et al., "Effects of Skin Occlusion on Percutaneous Absorption: An Overview," Skin Pharmacol. Appl. Skin Physiol., vol. 14, 2001, pp. 1-10.

\* cited by examiner
† cited by third party

PHARMACEUTICAL SPRAY COMPOSITION COMPRISING A VITAMIN D ANALOGUE AND A CORTICOSTEROID

CROSS REFERENCE

This is a continuation of application Ser. No. 16/135,366, filed Sep. 19, 2018, which is a continuation of application Ser. No. 14/707,733, filed May 8, 2015, now U.S. Pat. No. 10,130,640, which is a continuation of application Ser. No. 13/703,214, filed Jan. 28, 2013, now U.S. Pat. No. 9,119,781, which is a national stage entry under § 371 of PCT International Application No. PCT/DK2011/000060, filed Jun. 10, 2011, which claims the benefit of U.S. Provisional Application No. 61/353,893, filed Jun. 11, 2010, all of which are incorporated herein by reference.

FIELD OF INVENTION

The present invention relates to a topical spray composition comprising a biologically active vitamin D derivative or analogue and a corticosteroid, and its use in the treatment of dermal diseases and conditions.

BACKGROUND OF THE INVENTION

Psoriasis is a chronic inflammatory skin disease that manifests as erythematous, dry, scaling plaques resulting from hyperkeratosis. The plaques are most often found on the elbows, knees and scalp, though more extensive lesions may appear on other parts of the body, notably the lumbosacral region. The most common treatment of mild to moderate psoriasis involves topical application of a composition containing a corticosteroid as the active ingredient. While efficacious, application of corticosteroids has the disadvantage of a number of adverse effects such as skin atrophy, striae, acneiform eruptions, perioral dermatitis, overgrowth of skin fungus and bacteria, hypopigmentation of pigmented skin and rosacea.

For many years, however, an advantageous non-steroidal treatment of psoriasis has consisted in topical treatment with the vitamin D analogue compound, calcipotriol, formulated in an ointment composition (marketed as Daivonex® or Dovonex® ointment by LEO Pharma) in which the calcipotriol is present in solution or a cream composition (marketed as Daivonex® or Dovonex® cream by LEO Pharma). The solvent in the ointment composition is propylene glycol which has the advantage of enhancing penetration of the active ingredient into the skin, leading to an improved efficacy, but which is also known to act as a skin irritant. Thus, it has been reported that the inclusion of propylene glycol in topical compositions frequently causes patients to develop contact dermatitis (one study reported a number of irritant reactions to propylene glycol of 12.5%, cf. M. Hannuksela et al., *Contact Dermatitis* 1, 1975, pp, 112-116), and the number of irritant reactions increases when propylene glycol is used in high concentrations (as reviewed by J. Catanzaro and J. Graham Smith, *J. Am. Acad. Dermatol.* 24, 1991, pp. 90-95). Due to the improved penetration of calcipotriol into the skin resulting, inter alia, from the presence of propylene glycol, Daivonex® ointment has been found to be more efficacious in the treatment of psoriatic lesions than Daivonex® cream, but has also caused skin irritation in a significant proportion of psoriasis patients.

More recently, a combination product for the treatment of psoriasis has been marketed by LEO Pharma under the trade name Daivobet® ointment. The product comprises calcipotriol and betamethasone dipropionate as the active ingredients formulated in an ointment composition in which calcipotriol is dissolved in polyoxypropylene-15-stearyl ether and betamethasone dipropionate is present as a suspension. While the efficacy of the combination is significantly superior to that of either active ingredient on its own, the ointment may be perceived as cumbersome to apply as it requires prolonged rubbing into the skin of the affected area, and many patients, in particular those with extensive psoriatic lesions would favour a greater ease of application such as is provided by a spray composition. Daivobet® ointment does not contain any penetration enhancer such as propylene glycol which has been found to be detrimental to the chemical stability of calcipotriol (cf. example 2 of WO 00/64450). It is considered desirable to further improve the biological efficacy of the combination of the two active ingredients by providing a formulation vehicle from which penetration of the active ingredients into the skin is improved compared to the commercial product.

WO 00/64450 discloses a pharmaceutical composition comprising a vitamin D analogue and a corticosteroid formulated in a solvent containing vehicle in which both active ingredients are chemically stable. The preferred embodiment of the composition is an ointment and there is no mention of providing a spray composition with improved properties compared to an ointment.

US 2005/0281749 discloses a spray composition comprising a corticosteroid and a vitamin D derivative solubilised in an oily phase composed of one or more oils. The oil may be selected from a vegetable, mineral, animal, synthetic or silicone oil. There is no suggestion that it might be desirable to provide occlusion and consequently it is not proposed to add a semi-solid and occlusive excipient to the composition. There is no indication whether the composition exhibits improved penetration properties.

US 2005/0281754 discloses a spray composition comprising a corticosteroid and a vitamin D derivative formulated in a vehicle comprising an alcohol phase and an oil phase. The alcohol phase is composed of for instance ethanol, isopropanol or butanol. The oil phase may be composed of a mineral, vegetable or synthetic oil. There is no suggestion of including a semi-solid and occlusive excipient to the composition, and no indication whether the composition exhibits improved penetration properties.

SUMMARY OF THE INVENTION

It is an object of the invention to provide a topical spray composition comprising a vitamin D derivative or analogue and a corticosteroid as the active ingredients, which has skin penetration and biological activity properties superior to those of Daivobet® ointment but which contains a solvent for the active ingredients that unlike propylene glycol is not detrimental to the chemical stability of either the vitamin D derivative or analogue or the corticosteroid.

Human skin, in particular the outer layer, the stratum corneum, provides an effective barrier against penetration of microbial pathogens and toxic chemicals. While this property of skin is generally beneficial, it complicates the dermal administration of pharmaceuticals in that a large quantity, if not most, of the active ingredient applied on the skin of a patient suffering from a dermal disease may not penetrate into the viable layers of the skin where it exerts its activity. To ensure an adequate penetration of the active ingredient to the dermis and epidermis, it is generally preferred to include the active ingredient in a dissolved state, typically in the presence of a solvent in the form of an alcohol, e.g. ethanol, or diol, e.g. propylene glycol. Propylene glycol is a well-known penetration enhancer, i.e. a substance which is capable of penetrating the stratum corneum and "draw" low-molecular components such as therapeutically active components in the vehicle into the epidermis. Propylene glycol may in itself give rise to significant skin irritation, and it is also capable of "drawing" low-molecular and potentially irritative components of the vehicle into the epidermis, leading to an overall irritative effect of conventional vehicles including propylene glycol. For this reason, the presence of propylene glycol as a solvent in compositions intended for the treatment of inflammatory skin diseases may exacerbate the inflammatory response.

Another object of the invention is to provide a composition with improved penetration and biological activity of the active ingredients compared to Daivobet® ointment in the absence of conventional penetration enhancers such as propylene glycol which are detrimental to the stability of vitamin D compounds such as calcipotriol.

A further object of the invention is to provide a composition in which both the vitamin D derivative or analogue and the corticosteroid will not be significantly degraded. It is well known, e.g. from WO 00/64450 that vitamin D compounds are chemically unstable in acidic environments or in the presence of acid reacting components or impurities in the formulation vehicle. Likewise, it is well known that corticosteroids are chemically unstable in alkaline environments or in the presence of alkali reacting components or impurities in the formulation vehicle. In a composition comprising both ingredients the problem of chemical instability may not readily be solved by adding an acid or alkali neutralizing agent, respectively. On the contrary, care must be taken in the selection of excipients for inclusion in the composition such that no components are included which are detrimental to the chemical stability of either active ingredient.

Unlike the spray compositions disclosed in the references cited above, it is an object of the invention to provide a spray composition which contains significant amounts of an occlusive and semi-solid carrier excipient as the known oily spray formulations are more likely to spread to non-affected areas on application, whereas the semi-solid component makes the present composition less "runny" such that the active ingredients are preferentially applied on affected skin areas.

Thus, in one aspect the invention relates to a sprayable, storage stable, substantially anhydrous topical composition comprising a therapeutically effective amount of a vitamin D derivative or analogue and a therapeutically effective amount of a corticosteroid, the vitamin D derivative or analogue and the corticosteroid being dissolved in a pharmaceutically acceptable propellant selected from the group consisting of dimethyl ether, diethyl ether and methylethyl ether or a propellant mixture comprising a first propellant selected from the group consisting of dimethyl ether, diethyl ether and methylethyl ether and a second propellant selected from the group consisting of $C_{3-5}$ alkanes, hydrofluoroalkanes, hydrochloroalkanes, fluoroalkanes and chlorofluoroalkanes the composition further comprising a pharmaceutically acceptable lipid carrier solubilized or suspended in said propellant or propellant mixture, the lipid carrier comprising one or more lipids which on application on skin and evaporation of the propellant form a semi-solid and occlusive layer at the site of application.

The composition of the invention was surprisingly found to facilitate improved penetration of the active ingredients compared to the commercial Daivobet® ointment even in the absence of a conventional penetration enhancer. It is currently believed that improved penetration may be the result of the formation of a supersaturated solution of the active ingredients on the skin after application and evaporation of the propellant or propellant mixture (cf. Reid et al., *Pharm. Res.* 25(11), 2008, pp. 2573-2580). It is further believed that the propellant(s) themselves may act as penetration enhancers driving the active ingredients into the skin. Finally, the formation of a semi-solid and occlusive layer at the site of application may contribute to the penetration of the active ingredients.

In another aspect, the invention relates to a composition as disclosed herein for use in the treatment of dermatological diseases or conditions.

The compositions according to the invention may be dispensed from aerosol containers, typically of the type comprising a container body and valve assembly. The container body may, for instance, comprise a metal body, preferably lined with an chemically inert coating material to avoid degradation of the composition due to interaction between the body and the composition.

The valve assembly may comprise a valve cup, sometimes referred to as a mounting cup, a valve body or housing provided with a valve stem, a spring, a dip tube and an actuator. An inner gasket typically seals a hole in the valve stem, but when the actuator is operated the valve stem is shifted so that the hole is uncovered. Once exposed, the pressure exerted by the propellant in the container body forces the composition to flow through the hole into the dip tube and the valve stem and out through the actuator. As will be understood, when the actuator is released the valve spring returns the valve stem to the position where the hole is once again sealed.

The valve stem and actuator each contain one or more holes (orifices) and channels, the number, size and shape of which are determined in conjunction with the physical properties of the particular composition formulation so as to control both the flow rate through the valve and the characteristics of the spray that emerges from the actuator.

The spray pattern and flow rate may be controlled by means of a separate insert fitted into the outlet orifice of the actuator and which provides the terminal orifice for the actuator assembly. The channel through the insert leading to the outlet typically includes a portion narrower in diameter than the channel in the body of the actuator so that fluid emerging from the actuator channel into the insert channel is caused to swirl and break up into droplets. The insert may be profiled, for example it may be stepped, so that the composition is forced forwards and out of the terminal orifice in a forward motion, rather than the more usual rotational motion. This results in a homogeneous or solid spray pattern and hence enabling a user better to focus the composition on the area of skin being treated.

Since inhalation of the composition according to the invention is not desirable, it is preferred that the dimensions of the fluid channels, orifices, inserts, etc are selected to avoid production of a fine mist on expulsion.

The valve assembly may comprise a metering valve to permit only a metered quantity of the composition to be dispensed with each actuation of the actuator.

For storage, safety and/or hygiene reasons, the actuator may be provided with an protective hood or overcap, separate or integral therewith. The overcap may be moveable from a first position in which the terminal orifice is enclosed to a second position where the orifice is exposed; in the second position, the cover may also function as a directing nozzle by limiting the spray area. The actuator itself may comprise a simple button actuator, or may for example comprise a flip-top or twist-lock. In another arrangement, an overcap having an integral finger actuator may be secured to the container and cover an underlying actuator button. The underside of the overcap may include for example a plurality of projections for contacting the actuator button upon movement due to finger pressure of the operator and triggering the valve to open.

Alternatively, or in addition thereto, the actuator may be moveable between a first position in which the valve is prevented from being intentionally or accidentally operated and a second operative position. For example, part of the valve assembly may be rotatable about the valve stem such that in one rotary position the actuator is operable to dispense the product while in another rotary position the actuator aligns with projections or abutments on the container to prevent actuation. Such a "twist and spray" mechanism may include tactile or audible indications of the open and closed positions.

The inclusion of a tamper-evidence tab, which has to be broken before first use of the aerosol container, is desirable.

DETAILED DISCLOSURE OF THE INVENTION

Definitions

Figure 1A:
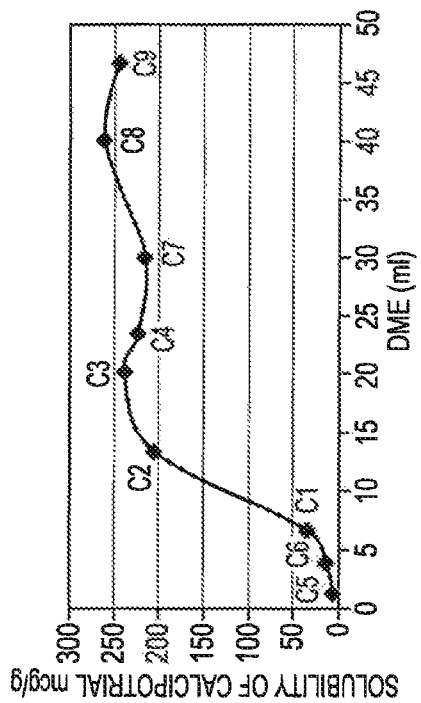
FIGS. 1a and 1b are graphs showing the solubility of calcipotriol in 100% dimethyl ether (DME) and in different ratios of DME and butane in the continuous phase (FIG. 1a) and in the mixture of continuous and dispersed phases (FIG. 1b).

The term "vitamin D derivative" is intended to indicate a biologically active metabolite of vitamin $D_3$, such as calcitriol, or a precursor to such a metabolite, such as alfacalcidol.

The term "vitamin D analogue" is intended to indicate a synthetic compound comprising a vitamin D scaffold with sidechain modifications and/or modifications of the scaffold itself. The analogue exhibits a biological activity on the vitamin D receptor comparable to that of naturally occurring vitamin D compounds.

"Calcipotriol" is a vitamin D analogue of the formula

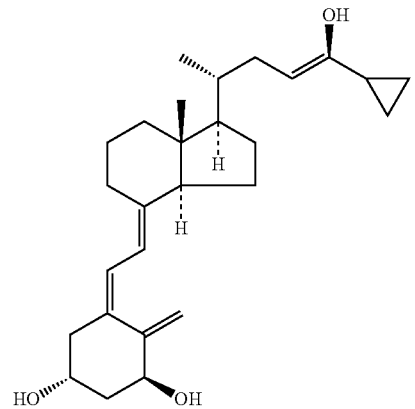

Calcipotriol has been found to exist in two crystalline forms, an anhydrate and a monohydrate. Calcipotriol monohydrate and its preparation are disclosed in WO 94/15912.

The term "storage stability" or "storage stable" is intended to indicate that the composition exhibits chemical and physical stability characteristics that permit storage of the composition for a sufficient period of time at refrigeration or, preferably, room temperature to make the composition commercially viable, such as at least 12 months, in particular at least 18 months, and preferably at least 2 years.

The term "chemical stability" or "chemically stable" is intended to mean that no more than 10%, preferably no more than 6%, of the active ingredients degrades over the shelf-life of the product, typically 2 years, at room temperature. An approximation of chemical stability at room temperature is obtained by subjecting the composition to accelerated stability studies at 40° C. where the composition is placed in a heating cupboard at 40° C. and samples are taken at 1, 2 and 3 months and tested for the presence of degradation products by HPLC. If less than about 10% of the substance has degraded after 3 months at 40° C., this is usually taken to correspond to a shelf-life of 2 years at room temperature. When the active ingredient included in the composition is calcipotriol, "chemical stability" usually indicates that the calcipotriol does not degrade significantly over time to 24-epi calcipotriol or other degradation products of calcipotriol in the finished pharmaceutical product.

The term "physical stability" or "physically stable" is intended to mean that the active ingredients do not precipitate from the propellant or vehicle phases over the shelf life of the composition.

The term "substantially anhydrous" is intended to mean that the content of free water in the ointment composition does not exceed about 2% by weight, preferably not about 1% by weight, of the composition.

The term "medium-chain triglycerides" is used to indicate triglyceride esters of fatty acids with a chain length of 6-12 carbon atoms. A currently favoured example of such medium chain triglycerides is a mixture of caprylic ($C_8$) and capric ($C_{10}$) triglycerides, e.g. available under the trade name Miglyol 812.

The term "solubilization capacity" is intended to indicate the ability of a solvent or mixture of solvents to dissolve a given substance, expressed as the amount required to effect complete dissolution of the substance.

The term "semi-solid" is used to denote a composition or excipient which shows viscoelastic behaviour and is non-Newtonian in character, i.e. does not flow at low shear stress, but exhibits plastic, pseudoplastic or thixotropic flow behaviour at high shear rates at room temperature. Typical examples of semi-solid compositions are ointments and creams.

The term "occlusive" is intended to indicate the provision of a lipid layer on the skin surface which forms a hydration barrier sufficient to result in reduction of transepidermal water loss, resulting in skin hydration.

The term "skin penetration" is intended to mean the diffusion of the active ingredient into the different layers of the skin, i.e. the stratum corneum, epidermis and dermis.

The term "skin permeation" is intended to mean the flux of the active ingredient through the skin into the systemic circulation or, in case of in vitro studies such as those reported in Example 4 below, the receptor fluid of the Franz cell apparatus used in the experiment.

The term "biological activity" is intended to mean the activity of a vitamin D derivative or analogue when applied to skin in a composition of the invention. The biological activity of compositions is determined in an in vitro assay measuring the activation of a target gene encoding cathelicidin in a reconstructed human epidermis model involving cultured human keratinocytes, as described in detail in Example 5 below.

Embodiments of the Invention

The vitamin D derivative or analogue included in the present composition may be selected from calcipotriol, calcitriol, tacalcitol, maxacalcitol, paricalcitol and alfacalcidol. A preferred vitamin D analogue which has been shown to be effective in the treatment of psoriasis is calcipotriol. Before dissolution in the solvent mixture, calcipotriol may be in the form of anhydrite or monohydrate, preferably the monohydrate.

The corticosteroid included in the present composition may be selected from the group consisting of amcinonide, betamethasone, budenoside, clobetasol, clobetasone, cortisone, desonide, desoxycortisone, desoximethasone, dexamethasone, diflucortolon, diflorasone, flucortisone, flumethasone, flunisolide, fluocinonide, fluocinolon, fluorometholone, fluprednisolone, flurandrenolide, fluticasone, halcinonide, halobetasol, hydrocortisone, meprednisone, methylprednisone, mometasone, paramethasone, prednicarbate, prednisone, prednisolone and triamcinolone or a pharmaceutically, acceptable ester or acetonide thereof. The corticosteroid may preferably be selected from betamethasone, budenoside, clobetasol, clobetasone, desoximethasone, diflucortolon, diflorasone, fluocinonide, fluocinolon, halcinonide, halobetasol, hydrocortisone, mometasone and triamcinolone or a pharmaceutically acceptable ester thereof. The corticosteroid ester may for instance be betamethasone acetate, betamethasone dipropionate, betamethasone valerate, clobetasol propionate, dexamethasone acetate, flumethasone pivalate, fluticasone propionate, hydrocortisone acetate, hydrocortisone butyrate or mometasone furoate. The acetonide may be selected from fluocinolone acetonide or triamcinolone acetonide.

The composition according to the invention may further comprise a non-evaporating oily co-solvent selected from at least one of the following solvent classes (a) a compound of general formula I $$H(OCH_2C(CH_3)H)_xOR^1$$

wherein $R^1$ is straight or branched chain $C_{1-20}$ alkyl, and x is an integer of 2-60;

(b) an isopropyl ester of a straight or branched chain $C_{10-18}$ alkanoic or alkenoic acid;

(e) a propylene glycol diester of a $C_{8-14}$ alkanoic or alkenoic acid;

(d) a straight or branched $C_{8-24}$ alkanol or alkenol;

(e) highly purified vegetable oils such as medium chain triglycerides or long chain triglycerides; and (f) N-alkylpyrrolidone or N-alkylpiperidone.

The oily co-solvent may serve to maintain the solubilization capacity of the composition on evaporation of the propellant or propellant mixture such that the active ingredients do not crystallize rapidly on the skin on evaporation of the propellant, but are present on the skin as a saturated solution from which they may penetrate into the skin (cf. Reid et al, *Pharm. Res.* 25 (11), 2008, pp. 2573-2580).

In one embodiment, the oily co-solvent included in the present composition may be a compound of general formula I such as polyoxypropylene-15-stearyl ether, polyoxypropylene-11-stearyl ether, polyoxypropylene-14-butyl ether, polyoxypropylene-10-cetyl ether or polyoxypropylene-3-myristyl ether.

In another embodiment, the oily co-solvent may be an isopropyl ester of a straight or branched chain $C_{10-18}$ alkanoic or alkenoic acid such as isopropyl myristate, isopropyl palmitate, isopropyl isostearate, isopropyl linolate or isopropyl monooleate.

In a further embodiment, the oily co-solvent may be a propylene glycol diester of a $C_{8-14}$ alkanoic acid such as propylene glycol dipelargonate.

In a still further embodiment, the oily co-solvent may be a straight $C_{8-24}$ alkanol, such as capryl, lauryl, cetyl, stearyl, oleyl, linoelyl or myristyl alcohol, or a branched $C_{8-24}$ alkanol, preferably $C_{18-24}$ alkanol, such as 2-octyldodecanol.

In a still further embodiment, the oily co-solvent is N-alkylpyrrolidone such as N-methylpyrrolidone.

In the research leading to the present invention, it was surprisingly found that using a pure $C_{3-5}$ alkane such as butane as the propellant did not lead to sufficient dissolution of the active ingredients so that the vitamin D analogue precipitated out of the solution with time and crystal growth of the corticosteroid was observed, i.e. the composition was not physically stable for the shelf-life of the composition. It was surprisingly found that this problem did not occur when dimethyl ether was used as the propellant on its own or even when a proportion of dimethyl ether was added to the $C_{3-5}$ alkane to form a propellant mixture. Thus, in a currently preferred embodiment the present composition comprises dimethyl ether as the sole propellant or as the first propellant of the propellant mixture.

In the present composition, the second propellant of the propellant mixture is favourably a $C_{3-5}$ alkane, preferably selected from the group consisting of n-propane, isopropane, n-butane or isobutane. A particularly favoured $C_{3-5}$ alkane is n-butane and/or isobutane.

In the propellant mixture, the ratio of n-butane and/or isobutane to dimethyl ether may favourably be in the range of 6:1-0:1 v/v, such as 5:1-1:2, 4:1-1:1, 4:2-1:1, 4:2-4:3 or 4:3-1:1.

In a particular embodiment, the composition comprises
 (a) about 0.00001-0.05% w/w of the vitamin D derivative or analogue,
 (b) about 0.0005-1% w/w of the corticosteroid,
 (c) about 5-55% w/w of the lipid carrier, and
 (d) about 45-95% w/w of the propellant or propellant mixture.

More specifically, the present composition may comprise about 10-50% w/w, about 15-45% w/w, or about 20-40% w/w of the lipid carrier.

More specifically, the present composition may comprise about 50-90% w/w or about 55-70% w/w of the propellant or propellant mixture.

In a specific embodiment, the present composition may further comprise about 0.1-10% w/w of the oily solvent as defined above, such as about 0.5-3% w/w, about 1-2.5% w/w or about 1.5-2% w/w of the oily solvent.

The lipid carrier may be a hydrocarbon or mixture of hydrocarbons With chain lengths ranging from $C_5$ to $C_{60}$. A frequently used ointment carrier is petrolatum, or white soft paraffin, which is composed of hydrocarbons of different chain lengths peaking at about $C_{40-44}$, or a mixture of petrolatum and liquid paraffin (consisting of hydrocarbons of different chain lengths peaking at $C_{28-40}$). While white soft paraffin provides occlusion of the treated skin surface, reducing transdermal loss of water and potentiating the therapeutic effect of the active ingredient in the composition, it tends to have a greasy or tacky feel which persists for quite some time after application. It may therefore be preferred to employ paraffins consisting of hydrocarbons of a somewhat lower chain length, such as paraffins consisting of hydrocarbons with chain lengths peaking at $C_{14-16}$, $C_{18-22}$, $C_{20-22}$, $C_{20-26}$ or mixtures thereof. It has been found that such paraffins are more cosmetically acceptable in that they are less greasy or tacky on application. The inclusion of such paraffins in the present composition is therefore expected to result in improved patient compliance. Suitable paraffins of this type, termed petrolatum jelly, are manufactured by Sonneborn and marketed under the trade name Sonnecone, e.g. Sonnecone CM, Sonnecone DM1, Sonnecone DM2 and Sonnecone HV, These paraffins are further disclosed and characterized in WO 2008/141078 which is incorporated herein by reference. In addition to their favourable cosmetic properties, it has surprisingly been found that compositions containing these paraffins as carriers are more tolerable than compositions containing conventional paraffins. (The hydrocarbon composition of the paraffins has been determined by gas chromatography). The lipid carrier may also be an isoparaffin such as isohexadecane.

The present composition may suitably include a lipophilic viscosity-increasing ingredient capable of imparting to the lipid carrier the property of forming a semi-solid and occlusive layer on skin after application and evaporation of the propellant. The lipophilic viscosity-increasing ingredient may suitably be a wax such as a mineral wax composed of a mixture of high molecular weight hydrocarbons, e.g. saturated $C_{35-70}$ alkanes, such as microcrystalline wax. Alternatively, the wax may be a vegetable or animal wax, e.g. esters of $C_{14-32}$ fatty acids and $C_{14-32}$ fatty alcohols, such as beeswax, a silicone wax or hydrogenated castor oil, or mixtures thereof. The amount of viscosity-increasing ingredient may typically be in the range of about 0.01-5% by weight of the composition. When the viscosity-increasing ingredient is hydrogenated castor oil it is typically present in an amount in the range of about 0.05-1% by weight, e.g. about 0.1-0.5% by weight, of the composition.

The composition may additionally comprise an emollient which may act to soften the thickened epidermis of the psoriatic plaques. A suitable emollient for inclusion in the present composition may be a volatile silicone oil as the presence of silicone has additionally been found to aid penetration of calcipotriol into the skin. Compositions including a silicone oil have also been found to result in less skin irritation. Suitable silicone oils for inclusion in the present composition may be selected from cyclomethicone and dimethicone. The amount of silicone oil included in the present composition is typically in the range of 0.3-3% w/w, such as about 0.5-1.5% w/w.

The present composition may also comprise other components commonly used in dermal formulations, e.g. antioxidants (e.g. alpha-tocopherol), preservatives, pigments, skin soothing agents, skin healing agents and skin conditioning agents such as urea, glycerol, allantoin or bisabolol, cf. *CTFA Cosmetic ingredients Handbook*, $2^{nd}$ Ed., 1992. In a favoured embodiment, the composition may comprise an anti-irritative agent such as menthol, eucalyptol or nicotinamide. A currently preferred anti-irritative agent is menthol as it has been found also to increase the penetration of calcipotriol into the skin, cf. FIG. 1. The menthol may be included in the composition in an amount of about 0.001-1% w/w, in particular about 0.002-0.003% w/w, of the composition.

The composition of the invention may be used in the treatment of psoriasis, sebopsoriasis, pustulosis palmoplantaris, dermatitis, ichtyosis, rosacea and acne and related skin diseases by topically administering an effective amount of a composition according to the invention to a patient in need of such treatment. Said method preferably comprises topical administration once or twice a day of a therapeutically sufficient dosage of said composition. To that end, the composition according to the invention preferably contains about 0.001-0.5 mg/g, preferably about 0.002-0.25 mg/g, in particular 0.005-0.05 mg/g, of the vitamin D derivative or analogue. It is envisaged that the present composition may advantageously be used for maintenance treatment of these dermal diseases, i.e. continued treatment after the disappearance of visible symptoms of the disease in order to delay recurrence of the symptoms.

In a further aspect, the invention relates to a pressurized container adapted to dispensing a topical composition on an affected skin area, the container comprising a composition according to the invention and a valve assembly and actuator for releasing the composition in the form of a spray.

Figures 6A, 6B:
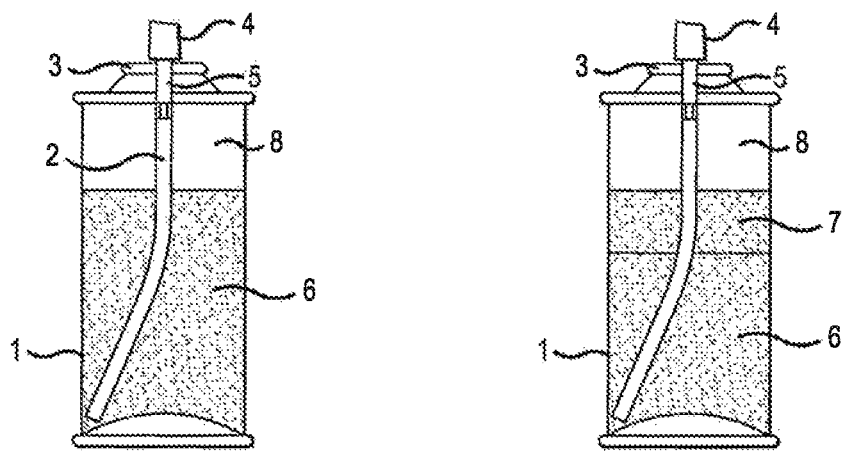
FIG. 6a shows a cross-section of a container intended for a pressurized spray composition of the invention, comprising a container body (1) onto which is fitted a valve assembly comprising a valve cup (3), a valve body (5), an actuator (4) and a dip tube (2). As shown in this embodiment, the present composition may be a two-phase system comprising a composition phase (6) and a vapor phase (8).
FIG. 6b shows a cross-section of a container intended for a pressurized spray composition of the invention, comprising a container body (1) onto which is fitted a valve assembly comprising a valve cup (3), a valve body (5), an actuator (4) and a dip tube (2). As shown in this embodiment, the present composition may be a three-phase system comprising a vehicle phase (6), a propellant phase (7) and a vapor phase (8).

As shown in FIGS. 6a and 6b, an example of a container suitable for a pressurized product may be composed of a container body (1) in which the present composition is stored, a dip tube (2), and a valve assembly comprising a valve cup (3), a valve body (5) and an actuator (4).

Typically, the container body (1) may be constructed from materials such as metal, glass, ceramics, polyester, polyethylene terephthalate (PET) or other polymer, or the like. Glass containers may be provided with a safety coating of for instance polypropylene to contain glass shards that may be formed on impact with a hard surface. Metal container bodies are currently preferred as they are better able to withstand impact and are amenable to surface coating. Stainless steel, tinplate and aluminium (i.e. aluminium or aluminium alloy, including anodised aluminium) container bodies are especially suitable materials for this purpose, with aluminium being currently preferred as it is light and not readily breakable.

Metal containers are typically lined or coated with an inert material to protect the composition from reactions with the metal, thereby preventing or substantially eliminating any degradation of the active ingredients or other components of the composition.

Inert materials include any suitable polymer, lacquer, resin or other coating treatment that creates a barrier between the container and the composition for preventing any chemical interaction between the composition and the container. Preferably the inert material is a non-metallic coating.

Known coatings for metal containers include acrylic, phenolic, polyester, epoxy and vinyl resins. However, a composition containing a vitamin D derivative or analogue, is likely to be chemically degraded under acidic conditions or in the presence of acidic reacting compounds. Moreover, corticosteroids are known to be chemically degraded under alkaline conditions or in the presence of alkaline reacting compounds. Accordingly, the container coating for use with a composition of the present invention should preferably be selected so that it exhibits no acidic or alkaline reactivity in itself, and that no acidic or alkaline reacting impurities are leached from it in the presence of the composition.

In the research leading to the present invention it was found, for example, that a particular epoxyphenol resin inner lacquer was incompatible with one of the active ingredients, causing unacceptable chemical degradation of calcipotriol. Such degradation may possibly be due to the presence in the lacquer of colophonium which includes an acid group. On the other hand, the chemical stability of calcipotriol was satisfactory when a polyimide-polyamide resin was used as the inner coating.

In addition to polyimide-polyamide coatings, other materials suitable for lining the interior of the metal containers include polyamides, polyimides, polypropylene, polyethylene, fluoropolymers, including perfluoroethylenepropylene copolymer (FEP), fluororubber (FPM), ethylene-propylene diene monomer rubber (EPDM), polytetrafluoroethylene (PTFE), ethylene tetrafluoroethylene copolymer (EFTE), perfluoroalkoxyalkanes, perfluoroalkoxyalkylenes, or blends of fluoropolymers with non-fluorocarbon polymers. Fluoropolymers may, for example, be used in combination with polyimide-polyamide resins.

The container coating material may be applied as a single layer, or in multiple layers, for example allowing each layer to cure before application of a further layer. As well as shielding the composition from the metal container, the application of more than one coating may also help prevent adhesion of the active ingredients on the container walls.

For the same reasons, valve components of the container that are brought into contact with the composition are also preferably made of, or coated with, materials that do not cause degradation of the composition. For example, metal valve components such as the valve cup may be coated with anodized silver, epoxymelamine or polypropylene.

As well as inhibiting leakage from the container, especially leakage of propellant, materials used for gaskets or seals within the container should also preferably be chemically inert. For example, the container body and valve cup may be crimped together using an intermediate gasket which at least in part is exposed to contact with the composition, thus if the gasket is not made of inert material it may over time result in degradation of the composition.

Extensive testing of materials used for gaskets in conventional aerosol container valves has established that polymeric materials prepared by vulcanization using sulphur-containing accelerators (e.g. thiazoles) are not suitable as gasket materials for containers intended to include the present composition, probably due to reactivity of sulphur-containing residues or impurities with one or both of the active ingredients resulting in chemical degradation.

Similarly, gasket materials permeable to the propellants included in the present composition are not suitable as gasket materials for the present purpose.

Suitable gasket or seal materials for use with compositions according the invention include fluoroelastomers (e.g, Viton V 600), fluorinated ethylene-propylene copolymer (FEP), fluororubber (FPM, e.g. VI500) or ethylene-propylene diene monomer rubber (EPDM).

Suitable materials for the dip tube has been found to be e.g. polyethylene and polypropylene. Suitable materials for the valve stem has been found to be e.g. polyamide and acetal (POM).

In the embodiment shown in FIG. 6b, the composition comprises a vehicle phase (6), a propellant phase (7) and a vapor phase (8). In this embodiment the spray container should be shaken thoroughly before use so that the vehicle phase (6) will be homogenously suspended in the propellant phase (7).

Figure 7:
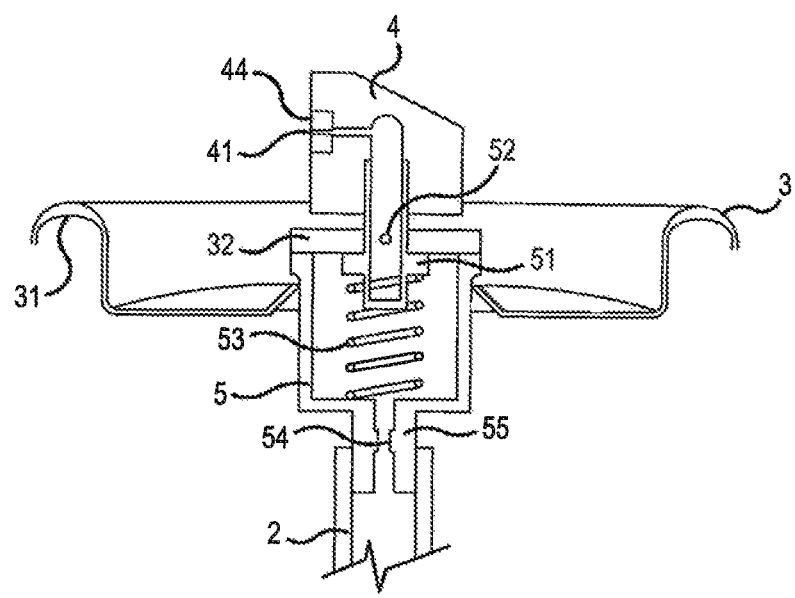
FIG. 7 shows a cross-section of a valve assembly to be mounted on the body of a container body (1), comprising a valve cup (3) provided with sealing (31) between the container body (1) and the valve cup (3) and a gasket (32), a valve body (5) provided with a valve stem (51) and a spring (53) connected to an actuator (4) provided with an insert (44) with a terminal orifice (41) through which the composition present in the container body (1) is expelled when the actuator (4) is depressed. The valve stem (51) contains an aperture (52) through which the composition present in the container body (1) may flow when the actuator is depressed. The valve body is further provided with a tailpiece (55) to which the dip tube (2) is connected. The tailpiece (55) is provided with an aperture (54) permitting the composition to flow from the dip tube (2).

As shown in FIG. 7, the valve assembly may be composed of a valve cup (3), which is typically made of metal such as aluminium, attached to the container body (1) by crimping, a valve body (5) which contains a valve stem (51) and a spring (53) connected to the actuator (4) which is depressed for activation to expel the composition from the container. The valve stem (51) contains at least one aperture (52) with a diameter of 0.05-1 mm through which the composition present in the container may flow when the actuator (4) is depressed. The valve stem aperture (52) may preferably be provided with a ball which allows the container to be used in different positions such as upside down or sideways.

The actuator (4) is provided with an insert (44) having a terminal orifice (41) with a diameter of 0.3-1.5 mm through which the composition is expelled. The actuator (4) should be designed so as to provide an aerosol spray from the orifice (41) with droplets of a size sufficiently small to ensure a uniform spray of the product, yet sufficiently large to ensure that the droplets of composition do not form a fine mist on expulsion from the container such that droplets containing biologically active substances may be accidentally inhaled.

The dimensions of the insert orifice (41) and valve stem aperture(s) (52) as well as the pressure within the container generally determine the width of the spray cone formed when the composition is expelled from the aperture (4) and consequently the size of the area that will be covered by the sprayed composition.

In a particular embodiment, the container may be provided with means for metering a dose of the composition.

The invention is further illustrated by the following examples which are not in any way intended to limit the scope of the invention as claimed.

EXAMPLES

Example 1

Testing the Solubility of Calcipotriol and BDP in Different Propellant Mixtures

2×12 100 ml glass bottles fitted with a valve and actuator were filled with compositions containing 67 mg BDP, 13 mg calcipotriol, 20 g vehicle (comprising liquid paraffin, white soft paraffin and PPG-15-stearyl ether) and varying amounts of DME and butane as shown in Table 1. The composition formed a continuous phase and a dispersed phase presumed to be composed of long-chain alkanes (with ≥50 carbon atoms in the chain) present in the white soft paraffin. The dispersed phase sedimented in the bottom portion of the composition on standing. Thus, the top portion of the composition contained only the continuous phase, while the bottom portion of the composition was composed of a mixture of continuous and dispersed phases.

TABLE 1

| Sample | DME (ml) | Butane (ml) |
|---|---|---|
| C1 | 6.7 | 40.0 |
| C2 | 13.3 | 33.3 |
| C3 | 20.0 | 26.7 |
| C4 | 23.3 | 23.3 |
| C5 | 1.3 | 45.3 |
| C6 | 4.0 | 42.7 |
| C7 | 30.0 | 16.7 |
| C8 | 40.0 | 6.7 |
| C9 | 46.7 | 0.0 |
| D1 | 6.7 | 40.0 |
| D2 | 13.3 | 33.3 |
| D3 | 20.0 | 26.7 |
| D4 | 23.3 | 23.3 |
| D5 | 1.3 | 45.3 |
| D6 | 4.0 | 42.7 |
| D7 | 30.0 | 16.7 |
| D8 | 40.0 | 6.7 |
| D9 | 46.7 | 0.0 |

C1-9 are samples taken from the continuous phase in the bottle
D1-9 are samples taken from the mixture of continuous and dispersed phases in the bottle Before sampling the bottles were shaken vigorously until the contents appeared to be homogenous after which the bottles were left overnight in the dark resulting in sedimentation of the dispersed phase in the bottom portion of the bottle in admixture with the continuous phase. Samples were taken from the top and bottom portions of the composition through a dip tube connected to the valve and reaching into the continuous phase or mixed continuous-dispersed phase, such that the sample of either phase was sprayed into a brown glass. Care was taken not to shake the bottles while handling so that the dispersed phase remained sedimented in the bottom portion of the composition. The sprayed samples were placed on a water bath at 40° C. for 5 hours until the propellant had evaporated. The samples were then cooled for 1 hour at room temperature.

The amount of calcipotriol and BDP present in each sample was determined by HPLC under the following operating conditions:

Column: Agilent Zorbas Eclipse Plus C18, 150×4.6 mm, 3.5 μm

Mobile phase: acetonitrile/methanol/0.01M $(NH_4)_2HPO_4$, pH 6.0, 25:45:30 (v/v/v)

Flow: 1.2 ml/min.

Detection: 225-320 nM. Calculation at 264 nm for calcipotriol and 240 nm for BDP Column oven: 30° C.

Auto sampler: 20° C.

Run time: 30 min.

Injection: 80 μl

Figure 1B:
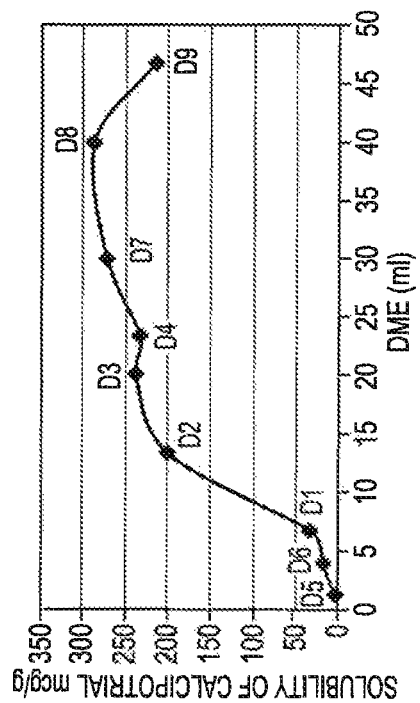
Figure 2A:
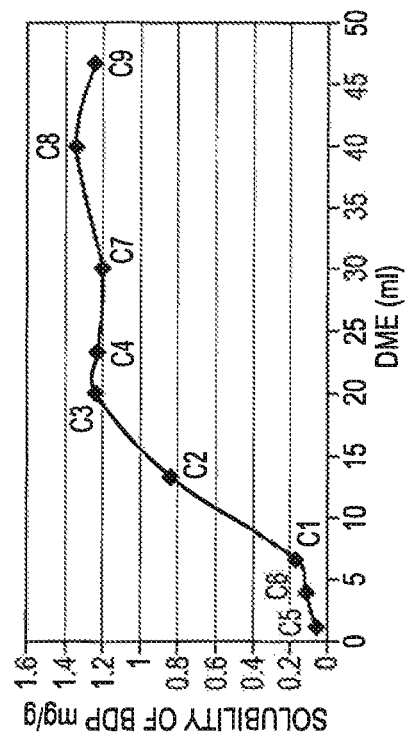
FIGS. 2a and 2b are graphs showing the solubility of betamethasone dipropionate (BDP) in 100% DME and in different ratios of DME and butane in the continuous phase (FIG. 2a) and in the mixture of the continuous and dispersed phases (FIG. 2b).
Figure 2B:
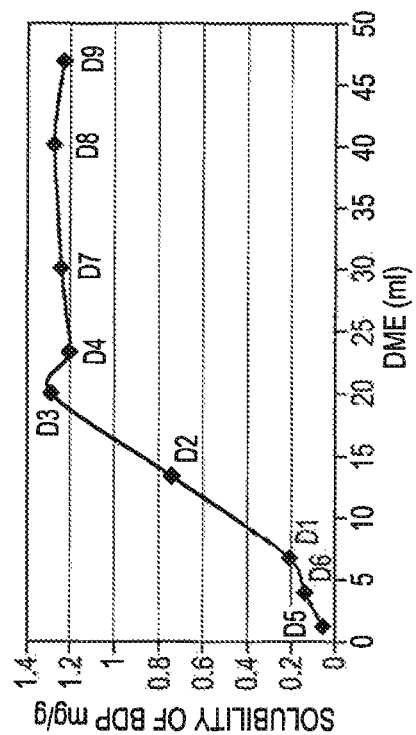

The results are shown in FIGS. 1a and 1b for calcipotriol and in FIGS. 2a and 2b for BDP. It appears from the figures that calcipotriol and BDP are both completely dissolved at a ratio of butane to DME of 4:3 in both the propellant and vehicle phases. Furthermore, it appears that calcipotriol and BDP are completely dissolved in 100% DME as the propellant.

The physical stability of calcipotriol and BDP in the composition was determined by polarized light microscopy. The results show that neither calcipotriol or BDP recrystallize when the compositions are left to stand for 4 months.

Example 2

Vehicle Compositions
Compositions A-E

To prepare Compositions A-E, white soft paraffin was melted at 80° C. followed by cooling to 70° C. and maintaining that temperature. Calcipotriol monohydrate was dissolved in polyoxypropylene-15-stearyl ether to form a solution which was added to the molten paraffin with stirring. BDP was dispersed in liquid paraffin and the dispersion was added to the calcipotriol-containing paraffin mixture with stirring, after which the mixture was cooled to below 30° C. 30 g portions of the mixture were transferred to aluminium spray containers provided with a polyamide-polyimide inner lacquer (HOBA 8460) after which a valve cup was fastened to the container body by crimping. The requisite amount of propellant mixture was added through a tube, after which the container was shaken for 5 minutes for complete dissolution of the calcipotriol and BDP,

| Ingredients | % w/w |
|---|---|
| Composition A | |
| Calcipotriol monohydrate | 0.002 |
| Betamethasone dipropionate | 0.026 |
| Liquid paraffin | 1.22 |
| α-tocopherol | 0.001 |
| PPG-15-stearyl ether | 2.0 |
| White soft paraffin | 37.5 |
| Dimethyl ether | 31.7 |
| Butane | 27.5 |
| Composition B | |
| Calcipotriol monohydrate | 0.002 |
| Betamethasone dipropionate | 0.02 |
| Liquid paraffin | 0.9 |
| α-tocopherol | 0.001 |
| PPG-15-stearyl ether | 1.6 |
| White soft paraffin | 28.9 |
| Dimethyl ether | 36.7 |
| Butane | 31.9 |
| Composition C | |
| Calcipotriol monohydrate | 0.001 |
| Betamethasone dipropionate | 0.006 |
| Liquid paraffin | 0.3 |

| Ingredients | % w/w |
| --- | --- |
| PPG-15-stearyl ether | 0.5 |
| White soft paraffin | 8.9 |
| Dimethyl ether | 90.3 |
| Composition D | |
| Calcipotriol monohydrate | 0.002 |
| Betamethasone dipropionate | 0.030 |
| Liquid paraffin | 1.42 |
| α-tocopherol | 0.001 |
| PPG-15-stearyl ether | 2.4 |
| White soft paraffin | 43.6 |
| Dimethyl ether | 52.6 |
| Composition E | |
| Calcipotriol monohydrate | 0.002 |
| Betamethasone dipropionate | 0.026 |
| Liquid paraffin | 1.22 |
| α-tocopherol | 0.001 |
| PPG-15-stearyl ether | 2.0 |
| White soft paraffin | 37.5 |
| Dimethyl ether | 27.5 |
| Butane | 31.7 |

Composition F

To prepare Composition F, hydrogenated castor oil is melted together with liquid paraffin at 85-90° C. and cooled with homogenisation to about 60° C. The mixture is then cooled to 25-30° C. with stirring. BDP is suspended in liquid paraffin and added to the homogenised mixture. Calcipotriol monohydrate is dissolved in polypropylene-15-stearyl ether and added to the mixture of the other ingredients, and the formulation was homogenised to ensure a homogenous distribution of the active ingredients. 30 g portions of the mixture are transferred to aluminium spray containers provided with a polyamide-polyimide inner lacquer (HOBA 8460) after which a valve cup is fastened to the container body by crimping. The requisite amount of propellant mixture is added through a tube, after which the container is shaken for 5 minutes for complete dissolution of the calcipotriol and BDP.

| Composition F Ingredients | % w/w |
| --- | --- |
| Calcipotriol monohydrate | 0.002 |
| Betamethasone dipropionate | 0.03 |
| PPG-15-stearyl ether | 6.6 |
| Hydrogenated castor oil | 0.8 |
| Liquid paraffin | 33.6 |
| Dimethyl ether | 27.3 |
| Butane | 31.7 |

Compositions G and H

To prepare composition G, a solution of calcipotriol monohydrate in N-methylpyrrolidone is mixed with medium chain triglycerides and polyoxypropylene-15-stearyl ether. Sonnecone DM1 and microcrystalline wax are melted at 80-85° C., and a solution of α-tocopherol in liquid paraffin is added at 80° C. with stirring until melting. After cooling to 70-75° C., the solvent mixture containing calcipotriol monohydrate is added with stirring. After cooling to about 40° C., menthol is added and the resulting mixture is stirred with cooling to below 30° C. 30 g portions of the mixture are transferred to aluminium spray containers provided with a polyamide-polyimide inner lacquer (HOBA 8460) after which a valve cup is fastened to the container body by crimping. The requisite amount of propellant mixture is added through a tube, after which the container is shaken for 5 minutes for complete dissolution of the calcipotriol and BDP,

| Composition G Ingredients | % w/w |
| --- | --- |
| Calcipotriol monohydrate | 0.002 |
| Betamethasone dipropionate | 0.03 |
| Medium chain triglycerides | 2.5 |
| N-methylpyrrolidone | 1.0 |
| PPG-15-stearyl ether | 0.6 |
| Menthol | 0.0025 |
| Liquid paraffin | 2.1 |
| α-tocopherol | 0.0025 |
| Petrolatum jelly white (Sonnecone DM1) | 30.3 |
| Microcrystalline wax (Multiwax 180 MH) | 4.1 |
| Dimethyl ether | 27.3 |
| Butane | 31.7 |

To prepare Composition H, white soft paraffin is melted at 80-85° C. and cooled to 70-75° C., and the solvent mixture is added with stirring. 30 g portions of the mixture is transferred to aluminium spray containers provided with a polyamide-polyimide inner lacquer (HOBA 8460) after which a valve cup is fastened to the container body by crimping. The requisite amount of propellant mixture is added through a tube, after which the container is shaken for 5 minutes for complete dissolution of the calcipotriol and BDP.

| Composition H Ingredients | % w/w |
| --- | --- |
| Calcipotriol monohydrate | 0.002 |
| Betamethasone dipropionate | 0.03 |
| Medium chain triglycerides | 2.5 |
| N-methylpyrrolidone | 1.0 |
| PPG-15-stearyl ether | 0.6 |
| White soft paraffin | 36.5 |
| Dimethyl ether | 27.3 |
| Butane | 31.7 |

Compositions I-P

Compositions I is prepared by mixing the medium chain triglycerides, caprylic/capric glycerides and polyoxyl 40 hydrogenated castor oil and stirring the mixture for 15 min. at 50° C. with a magnetic stirrer. The calcipotriol monohydrate is dissolved in the mixture at 40° C. using a magnetic stirrer for 15 min. White soft paraffin is melted at 80° C. The three-component surfactant-solvent mixture containing calcipotriol monohydrate is added to the melted paraffin and whisked until the ointment mixture is homogenous. The homogenized mixture is cooled to 30° C. with stirring. Composition is prepared in a similar fashion with the exception that glycerol monooleate 40 is used as the co-surfactant instead of caprylic/capric glycerides. 30 g portions of the mixture are transferred to aluminium spray containers provided with a polyamide-polyimide inner lacquer (HOBA 8460) after which a valve cup is fastened to the container body by crimping. The requisite amount of propellant mixture is added through a tube, after which the container is shaken for 5 minutes for complete dissolution of the calcipotriol and BDP.

| Ingredient (% w/w) | Comp. I | Comp. J |
|---|---|---|
| calcipotriol monohydrate | 0.002 | 0.002 |
| betamethasone dipropionate | 0.03 | 0.03 |
| medium chain triglycerides (Miglyol 812) | 1.1 | |
| long chain triglycerides (sesame oil) | | 1.1 |
| caprylic/capric glycerides (Akoline MCM) | 1.3 | |
| glycerol monooleate 40 (Peceol) | | 1.3 |
| polyoxyl 40 hydrogenated castor oil (Cremophor RH 40) | 1.8 | 1.8 |
| white soft paraffin | 31.2 | 31.2 |
| dimethyl ether | 36.2 | 36.2 |
| butane | 28.4 | 28.4 |

Compositions K-P are prepared in a similar fashion as composition I, but with appropriate substitution of the surfactant, co-surfactant and solvent as indicated in the table below.

| Ingredient (% w/w) | Comp. K | Comp. L | Comp. M | Comp. N | Comp. O | Comp. P |
|---|---|---|---|---|---|---|
| calcipotriol monohydrate | 0.002 | 0.002 | 0.002 | 0.002 | 0.002 | 0.002 |
| betamethasone dipripionate | 0.03 | 0.03 | 0.03 | 0.03 | 0.03 | 0.03 |
| lauroyl macrogol-6-glycerides (Labrafil M2130 CS) | 3.4 | 5.1 | 5.7 | 4.5 | 4.5 | 4.5 |
| polyglyceryl-3-diisostearate (Plurol Diisostearique) | 3.4 | | | | | |
| linoleyl macrogol-6-glyceride (Labrafil M2125CS) | | 1.7 | | | | |
| diethylene glycol monoethyl ether (Transcutol P) | | | 1.1 | | | |
| propylene glycol monolaurate (Lauroglycol 90) | | | | 2.3 | | |
| propylene glycol monocaprylate (Capryol 90) | | | | | 2.3 | |
| propylene glycol monocaprylate (Capryol 90) | | | | | | 2.3 |
| glycerol monocaprylocaprate (IMWITOR 742) | 0.4 | 0.4 | 0.4 | 0.4 | 0.4 | 0.4 |
| white soft paraffin | 30 | 30 | 30 | 30 | 30 | 30 |
| dimethyl ether | 34.3 | 34.3 | 34.3 | 34.3 | 34.3 | 34.3 |
| butane | 28.5 | 28.5 | 28.5 | 28.5 | 28.5 | 28.5 |

Example 3

Chemical Stability of Calcipotriol and BDP in Different Compositions

Composition E prepared as described in Example 2 above was stored in the spray containers for 3 months at 40° C. Samples of the composition were taken at 1, 2 and 3 months of storage, respectively, and the content of calcipotriol and BDP as well as possible degradation products (related impurities) was determined by HPLC. The results are shown in the Table below in percent of the theoretical initial value.

| | calcipotriol | | betamethasone dipropionate | |
|---|---|---|---|---|
| Sampling time | % of initial (theoretical) | % impurities | % of initial (theoretical) | % impurities |
| Initial analysis | 99.3 | 0.7 | 97.2 | 0.2 |
| 1 month | 95.1 | 2.0 | 95.6 | 0.2 |
| 2 months | 92.6 | 1.0 | 96.3 | 0.3 |
| 3 months | 93.6 | 1.9 | 96.7 | 0.5 |

It appears from the results that there is a discrepancy between the loss of calcipotriol after 3 months at 40° C. and the amount of impurities determined. This suggests that the apparent loss of calcipotriol is not the result of degradation of calcipotriol during storage, but may be ascribed to other causes such as, for instance, adsorption of calcipotriol to one or more of the container components, possibly the dip tube or inner lacquer. We have therefore concluded that both active ingredients are chemically stable under the stated conditions, suggesting that the composition may have a shelf life of about 2 years at 25° C.

Example 4

Penetration Studies

To investigate the skin penetration and permeation of calcipotriol from compositions of the invention, a skin diffusion experiment was conducted. Full thickness skin from pig ears was used in the study. The ears were kept frozen at −18° C. before use. On the day prior to the experiment the ears were placed in a refrigerator (5±3° C.) for slow defrosting. On the day of the experiment, the hairs were removed using a veterinary hair trimmer. The skin was cleaned of subcutaneous fat using a scalpel and two pieces of skin were cut from each ear and mounted on Franz diffusion cells in a balanced order.

Static Franz-type diffusion cells with an available diffusion area of 3.14 cm$^2$ and receptor volumes ranging from 8.6 to 11.1 ml were used in substantially the manner described by T. J. Franz, "The finite dose technique as a valid in vitro model for the study of percutaneous absorption in man", in *Current Problems in Dermatology*, 1978, J. W. H. Mall (Ed.), Karger, Basel, pp. 58-68. The specific volume was measured and registered for each cell. A magnetic bar was placed in the receptor compartment of each cell. After mounting the skin, physiological saline (35° C.) was filled into each receptor chamber for hydration of the skin. The cells were placed in a thermally controlled water bath which was placed on a magnetic stirrer set at 400 rpm. The circulating water in the water baths was kept at 35±1° C. resulting in a temperature of about 32° C. on the skin surface. After one hour the saline was replaced by receptor medium, 0.04 M isotonic phosphate buffer, pH 7.4 (35° C.), containing 4% bovine serum albumin. Sink conditions were maintained at all times during the period of the study, i.e. the concentration of the active compounds in the receptor medium was below 10% of the solubility of the compounds in the medium.

The in vitro skin permeation of each test composition was tested in 6 replicates (i.e. n=6). Each test composition was sprayed onto the skin membrane at 0 hours. A glass spatula was used to spread the composition evenly over the skin surface.

The skin penetration experiment was allowed to proceed for 21 hours. Samples were then collected from the following compartments at 2, 6 and 21 h:

The stratum corneum was collected by tape stripping 10 times using D-Squame® tape (diameter 22 mm, CuDerm Corp., Dallas, Tex., USA). Each tape strip is applied to the test area using a standard pressure for 5 seconds and removed from the test area in one gentle, continuous move. For each repeated strip, the direction of tearing off was varied. The viable epidermis and dermis was then sampled from the skin in a similar fashion.

Samples (1 ml) of the receptor fluid remaining in the diffusion cell were collected and analysed.

The concentration of calcipotriol in the samples were determined by LC mass spectrometry.

Figure 3:
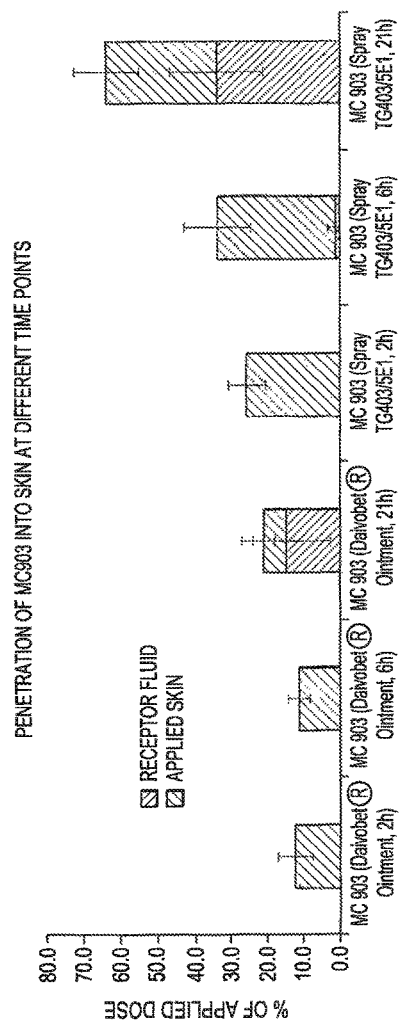
FIG. 3 is a graph showing the penetration of calcipotriol (MC 903) into viable skin from Composition E according to the invention at 2, 6 and 21 hours after application compared to the penetration of calcipotriol from Daivobet® ointment similarly applied.
Figure 4:
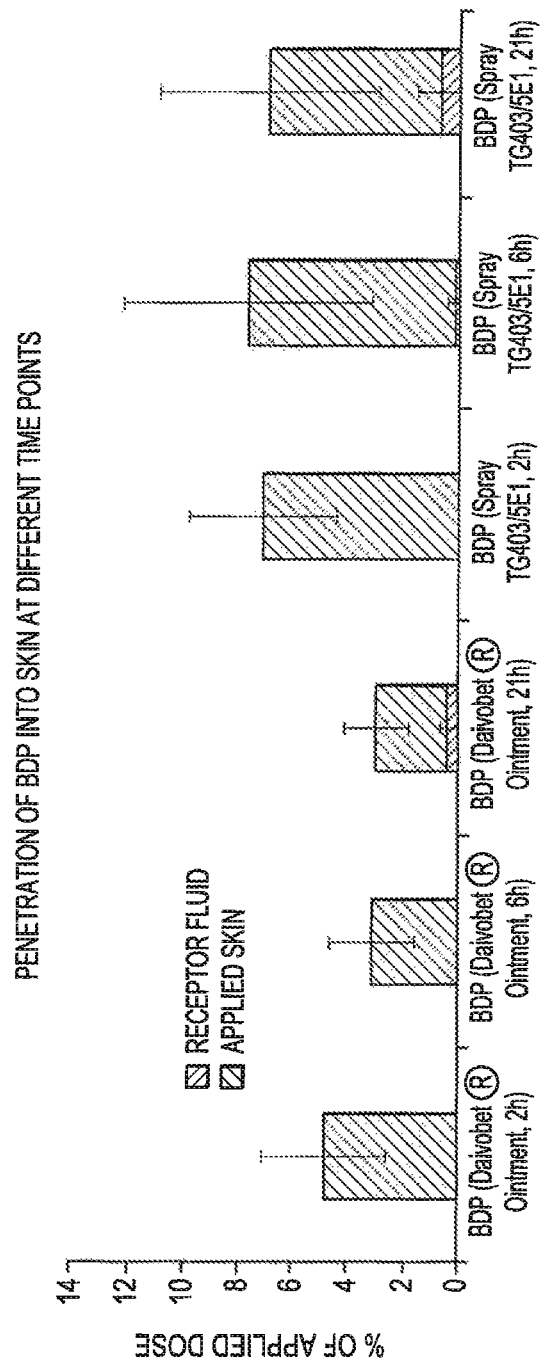
FIG. 4 is a graph showing the penetration of BDP into viable skin from Composition E according to the invention at 2, 6 and 21 hours after application compared to the penetration of BDP from Daivobet® ointment similarly applied.

The results appear from FIGS. 3 and 4 below which show the amount of calcipotriol and BDP, respectively, found in viable skin (dermis and epidermis) and receptor fluid in % of the applied dose 2, 6 and 21 hours after application. The results show that application of Composition E leads to a significant increase in skin permeation of calcipotriol and BDP compared to Daivobet® ointment.

Example 5

Biological Activity of the Compositions

Figure 5:
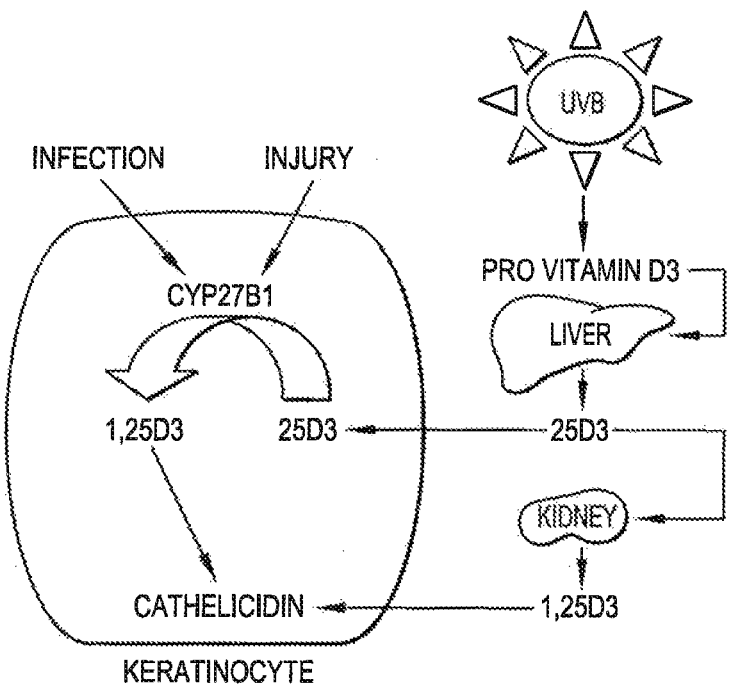
FIG. 5 is a schematic representation of the activation of the gene encoding cathelicidin by vitamin $D_3$ in human keratinocytes. The mechanism of cathelicidin gene activation is used in a biological assay using reconstructed human epidermis (human keratinocytes cultured so as to form the epidermal layers characteristic of human skin) on which calcipotriol-containing compositions of the invention are applied to activate cathelicidin as described in detail in Example 5 below.

As shown in FIG. 5 below, cathelicidin is an antimicrobial peptide expressed in human keratinocytes. The expression of cathelicidin is strongly induced on infection of the skin or disruption of the skin barrier. In psoriasis, the level of cathelicidin is increased in lesional skin of psoriasis patients. It has been found that the expression of the gene encoding cathelicidin may be induced by vitamin $D_3$ or vitamin D analogues such as calcipotriol (cf. T T Wang et al, *J. Immunol.* 173(5), 2004, pp. 2909-2912; J Schauber et al., *Immunology* 118(4), 2006, pp. 509-519; Schauber and Gallo, *J. Allergy Clin Immunol* 122, 2008, pp. 261-266; M. Peric et al., *PloS One* 4(7), Jul. 22, 2009, e6340) through binding to the vitamin D receptor. This finding has been utilized to develop an assay in which the uptake and biological activity of calcipotriol in human keratinocytes from the tested compositions has been determined by measuring the level of induction of the gene encoding cathelicidin.

In the assay, Composition E prepared as described in Example 2 above was sprayed topically in triplicate on reconstructed human epidermis consisting of normal human keratinocytes cultured for 12 days on 0.5 $cm^2$ polycarbonate filters (available from SkinEthic® Laboratories, Nice, France). The tissue was treated for two days followed by separation of the epidermis from the polycarbonate filter and snap-frozen in liquid nitrogen. RNA was extracted from the cells and cDNA synthesized by conventional procedures. Quantitative real-time PCR (qPCR) was then performed using the following assays from Applied Biosystems: CAMP Hs0018038_m1 and GAPDH Hs99999905_m1. The expression levels of cathelicidin were normalized to GAPDH and a relative quantification was made by comparison with Daivobet® ointment.

The results show a 2.3 fold increase in the biological activation of cathelicidin relative to that obtained with Daivobet® ointment.

Example 6

Chemical Stability of Calcipotriol/BDP in the Presence of Different Inner Lacquers Batches of Composition A prepared as described in Example 2 and placed in aluminium spray containers provided with two different types of inner lacquer, an epoxyphenol based lacquer (HOBA 7940/7407) and a polyimide-polyimide based lacquer (HOBA 8460), respectively, were tested for chemical stability of the active ingredients after standing for 1 month at 40° C. by spraying samples of each batch into a glass and subjecting them to HPLC by the procedure described in Example 3.

The results are shown in the table below.

| Batch # | Lacquer | Calcipotriol initial (µg/g) | Calcipotriol 1 m/40° C. (µg/g) | BDP (mg/g) initial | BDP (mg/g) 1 m/40° C. |
|---|---|---|---|---|---|
| 1 | EP | 48.7 | 24.5 | 0.626 | 0.606 |
| 2 | PI-PA | 50.8 | 48.6 | 0.632 | 0.623 |
| 3 | EP | 46.7 | 32.4 | 0.609 | 0.605 |
| 4 | PI-PA | 49.6 | 48.8 | 0.623 | 0.624 |
| 5 | EP | 48.4 | 23.5 | 0.610 | 0.603 |
| 6 | PI-PA | 50.2 | 48.7 | 0.627 | 0.625 |
| 7 | EP | 47.0 | 32.5 | 0.603 | 0.602 |
| 8 | PI-PA | 49.8 | 48.3 | 0.626 | 0.618 |
| 9 | EP | 47.8 | 27.6 | 0.611 | 0.602 |
| 10 | PI-PA | 49.3 | 48.1 | 0.619 | 0.617 |
| 11 | EP | 44.7 | 35.6 | 0.600 | 0.601 |
| 12 | PI-PA | 48.9 | 48.4 | 0.617 | 0.616 |

EP: epoxyphenol based lacquer
PI-PA: polyimide-polyamide based lacquer

It appears from the table that calcipotriol is unacceptably degraded when an epoxyphenol based lacquer is used as the inner lacquer of the spray container, while the chemical stability is acceptable in the presence of a polyimide-polyimide based inner lacquer. The chemical stability of betamethasone dipropionate appears to be much less affected by the composition of these inner lacquers. It is assumed that the degradation of calcipotriol shown in the table is caused by one or more acid reacting components in the epoxyphenol based HOBA 7940/7407 lacquer that may be leached from the lacquer due to the solvent action of the propellant mixture. It is currently assumed that such a component is colophonium as it includes an acid group.

Example 7

Testing the Solubility of Vitamin D Analogues and Corticosteroids in Different Propellant Mixtures 100 ml glass bottles fitted with a valve and actuator were filled with a compositions containing API (10 mg of calcitriol, tacalcitol, maxacalcitol, 30 mg clobetasol propionate, 60 mg betamethasone 17-valerate, hydrocortisone 17-butyrate, 120 mg hydrocortisone valerate or 800 mg hydrocortisone) and varying amounts of DME and butane (46.7 ml butane, 6.7 ml DME and 40.0 ml butane, or 23.3 ml DME and 23.3 ml butane) Before sampling the bottles were shaken vigorously until the contents appeared to be homogenous after which the bottles were left overnight in the dark resulting in sedimentation of the undissolved API. Samples were taken from the top of the composition through a dip tube connected to the valve, by spraying the sample into a scintillation glass. Care was taken not to shake the bottles while handling so that the undissolved API remained sedimented in the bottom portion of the composition. The API in the glass was dissolved in solvent for extraction and diluted if necessary before injected into the HPLC.

The amount of calcitriol, tacalcitol, maxacalcitol, betamethasone 17-valerate and clobetasol propionate present in each sample was determined by HPLC under the following operating conditions:

Column: 4.6×150 mm Waters Sunfire C18. 3.5 µm column
Mobile phase: Acetonitrile-methanol-water (20:50:30)
Flow: 1.2 ml/min.
Detection: PDA 210 nm-350 nm
Calculation for betamethasone 17-valerate and clobetasol propionate is done at 240 nm
Calculation for vitamin D analogues is done at 260 nm
Column oven: 35° C.
Auto sampler: 20° C.
Run time: 40 min.
Injection: Variable according to standard curve for each API
Retention time: 6.2 minutes (clobetasol propionate)
6.7 minutes (betamethasone 17-valerate)
10.5 minutes (maxacalcitol)
28.6 minutes (calcitriol)
32.6 minutes (tacacalcitol)

The amount of hydrocortosone, hydrocorticone-valerate and hyrdrocortisone 17-butyrate present in each sample was determined by HPLC under the following operating conditions:

Injection: Variable according to standard curve for each API
Column oven: 40° C.
Auto sampler: Ambient
Runtime; Minimum 4 times the retention time for hydrocortisone
Retention time: 6.0 minutes (hydrocortisone)
12.7 minutes (hydrocortisone 17-butyrate)
14.5 minutes (hydrocortisone valerate)

The results are shown in Table a and Table b for vitamin D analogues and corticosteroids, respectively. It appears from the Tables that the solubility of vitamin D analogues and corticosteroids increases by increasing the DME amount.

TABLE a

Solubility of vitamin D analogues at ambient temperature. Values are mean values from 2 determinations from the same bottle.

| DME in percent of total propellant | solubility (µg/g propellant) | | |
| --- | --- | --- | --- |
| (weight %) | calcitriol | tacalcitol | maxacalcitol |
| 0 | 14 | 24 | 32 |
| 16 | >250 | >250 | >300 |
| 53 | >250 | >250 | >300 |

TABLE b

Solubility of corticosteroids at ambient temperature. Values are mean values from 2 determinations from the same bottle.

| DME in % (by weight) of total propellant | Solubility (µg/g propellant) | | | | |
| --- | --- | --- | --- | --- | --- |
| | Betamethasone-17-valerate | Clobetasol propionate | Hydrocortisone 17-butyrate | Hydrocortisone valerate | Hydrocortisone |
| 0 | 3 | 5 | 3 | 9 | 5 |
| 16 | 73 | 133 | 68 | 154 | 8 |
| 53 | >1900 | >800 | >1600 | >3200 | 241 |

Column: Phenomenex Precolumn C18 4.0 mm×2.0 mm or equivalent+Waters
Sunfire C18 3.5 µm, 100 mm×4.6 mm or equivalent
Mobile phase: Eluent A: Tetrahydrofuran
Eluent B: Water

| | Time (min.) | Eluent A (%) | Eluent B (%) | Curve (Empower) |
| --- | --- | --- | --- | --- |
| Gradient: | 0.0 | 23 | 77 | — |
| | 6.0 | 23 | 77 | 11 |
| | 15.5 | 50 | 50 | 6 |
| | 23.0 | 23 | 77 | 1 |

Flow: 1.0 ml/min.
Pre column volume: Corresponding to the size of the loop
Detection: UV-254 nm
PDA-detector 220-320 nm Example 8

Chemical Stability of Calcipotriol/BDP in the Presence of Different Gasket Materials In order to test the compatibility of the composition with various gasket materials, samples were prepared with Composition E, see Example 2, filled in aluminum spray containers with a polyamide-polyimide inner lacquer and closed with a valve cup crimped to the container body. To each container, 10 pieces or an equivalent amount of gasket test material were added to the spray container and allowed to be submerged in the composition. The containers were stored at 25° C. or 40° C. and tested after 1 and 3 months at 40° C., and after 3 months at 25° C.

After storage, the composition was sprayed out in a glass bottle, and the propellants were allowed to evaporate for 2 days. The non-volatile part of the composition was analyzed for calcipotriol, betamethasone dipropionate and their related organic impurities.

The amount of calcipotriol was determined by HPLC after liquid extraction followed by a controlled isomerization at 50° C. Methyl testosterone was used as the internal standard. The following conditions were used for the HPLC analysis:

Column: LiChrospher RP-18, 125×4 mm, 5 µm
Mobile phase: Acetonitrile/methanol/0.01M $(NH_4)_2PO_4$ (20:50:30)
Flow: 2.0 ml/min
Detection: UV-264 nm
Injection: 50 µl
Run time: Approx. 9 minutes The organic impurities related to calcipotriol were determined by HPLC after liquid extraction, using the following conditions:

Column: YMC ODS-AM, 150×4.6 mm, 3 µm
Mobile phase: Acetonitrile/methanol/0.01M $(NH_4)_2PO_4$ (20:50:30)
Flow: 1.0 ml/min
Detection: UV-264 nm
Injection: 500 µl
Run time: 2 times the retention time of calcipotriol The amount of betamethasone dipropionate was determined by HPLC after liquid extraction, using beclomethasone dipropionate as internal standard and the following HPLC conditions:

Column: Superspher RP-18, 75×4 mm, 4 µm
Mobile phase: Acetonitrile/water (50:55)
Flow: 1.5 ml/min
Detection: UV-240 nm
Injection: 20 µl
Run time: Approx. 9 minutes The organic impurities related to betamethasone dipropionate were extracted by liquid extraction and analyzed by HPLC using the following conditions:

Column: LiChrospher RP-18, 125×4 mm, 5 µm
Mobile phase: Acetonitrile/0.05M $(NH_4)_2PO_4$ pH 7 (50:55)
Flow: 2.0 ml/min
Detection: UV-240 nm
Injection: 20 µl
Run time: Approx. 20 minutes The results are presented in the table below:

| Gasket type | Temp/ months | Calcipotriol (µg/g) | BDP (mg/g) | 5,6-Trans-calcipotriol (area-%) | 24-Epi-calcipotriol (area-%) |
|---|---|---|---|---|---|
| Buna | 40° C./1 m | 40.2 | 0.557 | 4.3 | 0.9 |
|  | 40° C./3 m | 27.3 | 0.555 | 6.3 | 1.3 |
|  | 25° C./3 m | 42.5 | 0.559 | 2.6 | 0.8 |
| Viton | 40° C./1 m | 48.9 | 0.610 | 0.4 | 0.6 |
|  | 40° C./3 m | 48.7 | 0.607 | 0.6 | 0.6 |
|  | 25° C./3 m | 49.8 | 0.607 | 0.2 | 0.5 |
| NPR | 40° C./1 m | 44.1 | 0.554 | 0.3 | 4.7 |
|  | 40° C./3 m | 38.4 | 0.549 | 0.3 | 9.6 |
|  | 25° C./3 m | 46.6 | 0.535 | 0.1 | 2.9 |
| EPDM | 40° C./1 m | 49.2 | 0.641 | 0.5 | 0.7 |
|  | 40° C./3 m | 47.6 | 0.611 | 1.0 | 0.9 |
|  | 25° C./3 m | 49.5 | 0.616 | 0.4 | 0.8 |

Buna and NPR are nitrile rubbers, Viton is a fluoroelastomer, and EPDM is a ethylene-propylene diene monomer rubber.

The data show that two of the gasket types, Buna and NPR, resulted in decomposition of both calcipotriol and betamethasone dipropionate. Based on this compatibility test, it was concluded that these two materials were not suitable for use in contact with the tested composition. The Viton and EPDM gaskets did not have negative impact on the stability of calcipotriol and betamethasone dipropionate and they are therefore considered to be useful as gasket materials for the composition tested.

The invention claimed is:

1. A sprayable, substantially anhydrous topical composition comprising
    calcipotriol or calcipotriol monohydrate,
    betamethasone dipropionate,
    a pharmaceutically acceptable propellant, present in amount between 45-95% w/w of the total composition,
    a pharmaceutically acceptable lipid carrier, present in an amount between 5-55% w/w of the total composition, and
    a pharmaceutically acceptable antioxidant,
    wherein the composition does not include propylene glycol,
    wherein visible crystals of the calcipotriol or calcipotriol monohydrate or the betamethasone dipropionate are not observed, as determined by polarized light microscopy, after storage of the composition for 12 months at about 25° C.

2. The composition of claim 1, wherein each gram of the composition, excluding any mass contributed by any pharmaceutically acceptable propellant, comprises 52.2 mcg of calcipotriol monohydrate and 0.643 mg betamethasone dipropionate.

3. The composition of claim 2, wherein the composition further comprises a pharmaceutically acceptable lipophilic viscosity increasing ingredient.

4. The composition of claim 1, wherein the pharmaceutically acceptable propellant comprises a $C_{3-5}$ alkane.

5. The composition of claim 4, wherein the $C_{3-5}$ alkane is propane, isopropane, n-butane, isobutane, or mixtures thereof.

6. The composition of claim 5, wherein the $C_{3-5}$ alkane is n-butane.

7. The composition of claim 2, wherein the pharmaceutically acceptable propellant comprises dimethyl ether.

8. The composition of claim 1, wherein the pharmaceutically acceptable lipid carrier comprises petrolatum.

9. The composition of claim 8, wherein the composition further comprises a pharmaceutically acceptable oily co-solvent.

10. The composition of claim 9, wherein the oily co-solvent comprises a compound of general formula I: $H(OCH_2C(CH_3)H)_xOR^1$ wherein $R^1$ is a straight or branched chain $C_{1-20}$ alkyl, and x is an integer from 2 to 60 inclusive.

11. The composition of claim 10, wherein the compound of general formula I is polyoxypropylene-15-stearyl ether, polyoxypropylene-11-stearyl ether, polyoxypropylene-14-butyl ether, polyoxypropylene-10-cetyl ether, or polyoxypropylene-3-myristyl ether.

12. The composition of claim 9, wherein the oily co-solvent comprises an isopropyl ester of a straight or branched chain $C_{10-18}$ alkanoic or alkenoic acid.

13. The composition of claim 12, wherein the isopropyl ester of a straight or branched chain $C_{10-18}$ alkanoic or alkenoic acid is isopropyl myristate, isopropyl palmitate, isopropyl isostearate, isopropyl linolate, or isopropyl monooleate.

14. The composition of claim 9, wherein the oily co-solvent comprises a straight or branched $C_{8-24}$ alkanol or alkenol.

15. The composition of claim 14, wherein (i) the straight $C_{8-24}$ alkanol is capryl alcohol, lauryl alcohol, cetyl alcohol, stearyl alcohol, or myristyl alcohol, (ii) the straight $C_{8-24}$ alkenol is oleyl alcohol or linoleyl alcohol, and/or (iii) the branched $C_{8-24}$ alkanol is a branched $C_{18-24}$ alkanol.

16. The composition of claim 15, wherein the straight $C_{8-24}$ alkanol is myristyl alcohol.

17. The composition of claim 9, wherein
the calcipotriol or calcipotriol monohydrate is present in an amount between 0.001-0.05% w/w of the total composition,
the betamethasone dipropionate is present in an amount between 0.0005-1% w/w of the total composition, and
the pharmaceutically acceptable oily co-solvent is present in an amount between 0.1-10% w/w of the total composition.

18. The composition of claim 17, wherein the composition comprises calcipotriol, wherein
the calcipotriol is present in an amount of 0.005% w/w of the composition, excluding any mass contributed by any pharmaceutically acceptable propellant, and
the betamethasone dipropionate is present in an amount of 0.064% w/w of the composition, excluding any mass contributed by any pharmaceutically acceptable propellant.

19. The composition of claim 17, wherein the composition comprises calcipotriol monohydrate, wherein
the calcipotriol monohydrate is present in an amount of 0.00522% w/w of the composition, excluding any mass contributed by any pharmaceutically acceptable propellant, and
the betamethasone dipropionate is present in an amount of 0.064% w/w of the composition, excluding any mass contributed by any pharmaceutically acceptable propellant.

20. The composition of claim 19 wherein the pharmaceutically acceptable oily co-solvent is myristyl alcohol.

21. The composition of claim 2, wherein the pharmaceutically acceptable propellant comprises dimethyl ether; the pharmaceutically acceptable lipid carrier is a mixture of liquid paraffin and petrolatum.

22. The composition of claim 21, further comprising a pharmaceutically acceptable oily co-solvent.

23. The composition of claim 1, wherein visible crystals of the calcipotriol or calcipotriol monohydrate or the betamethasone dipropionate have not formed after storage of the composition for 18 months at about 25° C.

24. The composition of claim 1, wherein visible crystals of the calcipotriol or calcipotriol monohydrate or the betamethasone dipropionate have not formed after storage of the composition for 24 months at about 25° C.

25. The method of treatment of claim 8, wherein the petrolatum is white soft paraffin.

26. The method of treatment of claim 21, wherein the petrolatum is white soft paraffin.

* * * * *

UNITED STATES PATENT AND TRADEMARK OFFICE
CERTIFICATE OF CORRECTION

PATENT NO. : 10,716,799 B2
APPLICATION NO. : 16/554586
DATED : July 21, 2020
INVENTOR(S) : Marianne Lind et al.

It is certified that error appears in the above-identified patent and that said Letters Patent is hereby corrected as shown below:

In the Claims

Claim 25, Column 26, Line 22, "The method of treatment of claim 8," should read -- The composition of claim 8, --.

Claim 26, Column 26, Line 24, "The method of treatment of claim 21," should read -- The composition of claim 21, --.

Signed and Sealed this
Fifteenth Day of September, 2020

Andrei Iancu
*Director of the United States Patent and Trademark Office*